US009789184B2

(12) United States Patent
Daly et al.

(10) Patent No.: US 9,789,184 B2
(45) Date of Patent: Oct. 17, 2017

(54) ANTI-EGFR ANTIBODIES AND USES THEREOF

(71) Applicant: Regeneron Pharmaceuticals, Inc., Tarrytown, NY (US)

(72) Inventors: Christopher Daly, New York, NY (US); Gavin Thurston, Briarcliff Manor, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 99 days.

(21) Appl. No.: 14/820,324

(22) Filed: Aug. 6, 2015

(65) Prior Publication Data
US 2015/0337043 A1 Nov. 26, 2015

Related U.S. Application Data

(62) Division of application No. 13/925,923, filed on Jun. 25, 2013, now Pat. No. 9,132,192.

(60) Provisional application No. 61/821,000, filed on May 8, 2013, provisional application No. 61/663,984, filed on Jun. 25, 2012.

(51) Int. Cl.
*A61K 39/395* (2006.01)
*A61K 45/06* (2006.01)
*C07K 16/28* (2006.01)
*A61K 39/00* (2006.01)

(52) U.S. Cl.
CPC .... *A61K 39/39558* (2013.01); *A61K 39/3955* (2013.01); *A61K 45/06* (2013.01); *C07K 16/2863* (2013.01); *A61K 2039/505* (2013.01); *A61K 2039/507* (2013.01); *C07K 2317/21* (2013.01); *C07K 2317/565* (2013.01); *C07K 2317/73* (2013.01); *C07K 2317/732* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,943,533 | A | 7/1990 | Mendelsohn |
| 5,844,093 | A | 12/1998 | Kettleborough |
| 7,060,808 | B1 | 6/2006 | Goldstein |
| 7,247,301 | B2 | 7/2007 | van de Winkel |
| 7,595,378 | B2 | 9/2009 | van de Winkel |
| 7,662,374 | B2 | 2/2010 | Greene |
| 7,723,484 | B2 | 5/2010 | Beidler |
| 7,939,072 | B2 | 5/2011 | Yarden |
| 2010/0305307 | A1 | 12/2010 | Jakobovits et al. |

FOREIGN PATENT DOCUMENTS

| WO | WO 2004/008099 | 1/2004 |
| WO | WO 2005/079434 | 9/2005 |
| WO | WO 2010/108127 | 9/2010 |

OTHER PUBLICATIONS

Bonner, et al. (2006) New England Journal of Medicine 354: 567-578, "Radiotherapy plus Cetuximab for Squamous-Cell Carcinoma of the Head and Neck".
Capdevila, et al. (2009) Cancer Treatment Reviews 35: 354-363, "Anti-epidermal growth factor receptor monoclonal antibodies in cancer treatment".
Cunningham, et al. (2004) New England Journal of Medicine 351: 337-345, "Cetuximab Monotherapy and Cetuximab plus Irinotecan in Irinotecan-Refractory Metastatic Colorectal Cancer".
Goffin and Zbuk (2013) Clinical Therapeutics 35(9): 1282-1303, "Epidermal Growth Factor Receptor: Pathway, Therapies, and Pipeline".
Takeuchi and Ito (2011) Biol. Pharm. Bull. 34(12): 1774-1780, "Receptor Tyrosine Kinases and Targeted Cancer Therapeutics".
Van Cutsem, et al. (2009) New England Journal of Medicine 360(14):1408-1417, "Cetuximab and Chemotherapy as Initial Treatment for Metastatic Colorectal Cancer".
Cai, et al. (2008) Oncogene 27(27): 3870-3874, "Differential binding patterns of monoclonal antibody 2C4 to the ErbB3-p185(her2/neu) and the EGFR-p185(her2/neu) complexes".
Gajadhar, et al. (2012) Molecular Cancer Research 10(3): 428-440, "In Situ Analysis of Mutant EGFRs Prevalent in Glioblastoma Multiforme Reveals Aberrant Dimerization, Activation, and Differential Response to Anti-EGFR Targeted Therapy".
Communication Relating to the Results of the Partial International Search (Annex to Form PCT/ISA/206 dated Oct. 17, 2013) for corresponding International Application No. PCT/US13/47476.
Wu, et al. (1999) Journal of Molecular Biology 294:151-162, "Humanization of a murine monoclonal antibody by simultaneous optimization of framework and CDR residues".
Skolnick and Fetrow (2000) Trends in Biotechnology 18:34-39, "From genes to protein structure and function: novel applications of computational approaches in the genomic era".
Vajdos, et al. (2002) Journal of Molecular Biology 320:415-428, "Comprehensive functional maps of the antigen-binding site of an anti-ErbB2 antibody obtained with shotgun scanning mutagenesis".
Casset, et al. (2003) Biomechanical and Biophysical Research Communication 307:198-205, "A peptide mimetic of an anti-CD4 monoclonal antibody by rational design".
Bendig, Mary M., (1995) Methods: A Companion to Methods in Enzymology 8:83-93, "Humanization of Rodent Monoclonal Antibodies by CDR Grafting".

(Continued)

*Primary Examiner* — Michael Pak
(74) *Attorney, Agent, or Firm* — Swanson & Bratschun, L.L.C.

(57) ABSTRACT

The present invention provides antibodies that bind to EGFR and methods of using same. According to certain embodiments of the invention, the antibodies are fully human antibodies that bind to human EGFR with high affinity. In certain embodiments, the antibodies of the present invention are capable of inhibiting the growth of tumor cells expressing high levels of EGFR and/or inducing antibody-dependent cell-mediated cytotoxicity (ADCC) of such cells. The antibodies of the invention are useful for the treatment of various cancers as well as other EGFR-related disorders.

13 Claims, No Drawings

(56) References Cited

OTHER PUBLICATIONS

Paul, E. William, M.D., (1993) Raven Press New York, 3rd Edition (textbook), Fundamental Immunology, "Fv Structure and Diversity in Three Dimensions" pp. 292-295.
MacCullum et al. (1996) Journal of Molecular Biology 262: 732-745, "Antibody-antigen Interactions: Contact Analysis and Binding Site Topography".
First Examination Report dated Aug. 31, 2016 for corresponding New Zealand Application No. 701633.

ANTI-EGFR ANTIBODIES AND USES THEREOF

CROSS-REFERENCE TO RELATED APPLICATIONS

This application is a divisional of U.S. patent application Ser. No. 13/925,923 filed Jun. 25, 2013, entitled "Anti-EGFR Antibodies and Uses Thereof," which claims the benefit under 35 U.S.C. §119(e) of US provisional application Nos. 61/663,984, filed on Jun. 25, 2012; and 61/821,000, filed on May 8, 2013, the disclosures of which are herein incorporated by reference in their entireties.

FIELD OF THE INVENTION

The present invention relates to antibodies, and antigen-binding fragments thereof, which are specific for human EGFR, and methods of use thereof.

BACKGROUND

Epidermal growth factor receptor (EGFR, also known as HER1 or ErbB1) is a member of the ErbB/HER family of type 1 receptor tyrosine kinases (RTKs). Other members of this family include ErbB2 (HER2 or Neu), ErbB3 (HER3) and ErbB4 (HER4). Known ligands for EGFR include epidermal growth factor (EGF) and transforming growth factor alpha (TGF-α). Ligand binding to EGFR induces tyrosine phosphorylation and receptor dimerization with other ErbB family members.

RTKs such as EGFR function to allow cells to respond to diverse external stimuli. However, aberrant activation and/or overexpression of EGFR is associated with the development and progression of several human cancers. Accordingly, EGFR is a target for anti-cancer therapies. Approved drugs targeting EGFR include small molecule inhibitors such as gefitinib (Iressa®) and erlotinib (Tarceva®), and anti-EGFR antibodies such as cetuximab (Erbitux®) and panitumumab (Vectibix®). Anti-EGFR antibodies are mentioned in, e.g., U.S. Pat. No. 4,943,533, U.S. Pat. No. 5,844,093, U.S. Pat. No. 7,060,808, U.S. Pat. No. 7,247,301, U.S. Pat. No. 7,595,378, U.S. Pat. No. 7,723,484, and U.S. Pat. No. 7,939,072. Nonetheless, there is a need in the art for novel EGFR antagonists, such as anti-EGFR antibodies, for the treatment of cancer and other related disorders.

BRIEF SUMMARY OF THE INVENTION

The present invention provides antibodies that bind human EGFR. The antibodies of the invention are useful, inter alia, for inhibiting EGFR-mediated signaling and for treating diseases and disorders caused by or related to EGFR activity and/or signaling. The antibodies of the invention are also useful for inducing cell death in cells that express high levels of EGFR on their surfaces.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides antibodies, or antigen-binding fragments thereof comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, and 370, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, and 378, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, and 376, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, and 384, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, and 376/384.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, and 372, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, and 374, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, and 380, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, and 382, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M085N); 20-22-24-28-30-32 (e.g. H1M086N); 36-38-40-44-46-48 (e.g. H1M089N); 52-54- 56-60-62-64 (e.g. H1M102N); 68-70-72-76-78-80 (e.g. H1M103N); 84-86-88-92-94-96 (e.g. H1M116N); 100-102-104-108-110-112 (e.g. H1H134P); 116-118-120-124-126-128 (e.g. H1H136P); 132-134-136-140-142-144 (e.g. H1H141P); 148-150-152-156-158-160 (e.g., H1H142P); 164-166-168-172-174-176 (e.g. H1H143P); 180-182-184-188-190-192 (e.g., H1H144P); 196-198-200-204-206-208 (e.g. H1H145P); 212-214-216-220-222-224 (e.g. H1H147P); 228-230-232-236-238-240 (e.g. H1H151P); 244-246-248-252-254-256 (e.g. H1H153P); 260-262-264-268-270-272 (e.g. H1H155P); 276-278-280-284-286-288 (e.g. H1H157P); 292-294-296-300-302-304 (e.g. H1H158P); 308-310-312-316-318-320 (e.g. H1H159P); 324-326-328-332-334-336 (e.g. H1H161P); 340-342-344-348-350-352 (e.g. H1H163P); 356-358-360-364-366-368 (e.g. H1H169P); and 372-374-376-380-382-384 (e.g. H1H171P).

In a related embodiment, the invention includes an antibody or antigen-binding fragment of an antibody which specifically binds EGFR, wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, and 370/378. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-EGFR antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, and 369, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, and 377, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, and 375, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, and 383, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, and 371, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, and 373, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, and 379, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, and 381, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H1M085N), 17 and 25 (e.g. H1M086N), 33 and 41 (e.g. H1M089N), 49 and 57 (e.g. H1M102N), 65 and 73 (e.g. H1M103N), 81 and 89 (e.g. H1M116N), 97 and 105 (e.g. H1H134P), 113 and 121 (e.g. H1H136P), 129 and 137 (e.g. H1H141P), 145 and 153 (e.g. H1H142P), 161 and 169 (e.g. H1H143P), 177 and 185 (e.g. H1H144P), 193 and 201 (e.g. H1H145P), 209 and 217 (e.g. H1H147P), 225 and 233 (e.g. H1H151P), 241 and 249 (e.g. H1H153P), 257 and 265 (e.g. H1H155P), 273 and 281 (e.g. H1H157P), 289 and 297 (e.g. H1H158P), 305 and 313 (e.g. H1H159P), 321 and 329 (e.g. H1H161P), 337 and 345 (e.g. H1H163P), 353 and 361 (e.g. H1H169P), or 369 and 377 (e.g. H1H171P).

The present invention includes anti-EGFR antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds EGFR and a pharmaceutically acceptable carrier. In a related aspect, the invention features a composition which is a combination of an anti-EGFR antibody and a second therapeutic agent. In one embodiment, the second therapeutic agent is any agent that is advantageously combined with an anti-EGFR antibody. Exemplary agents that may be advantageously combined with an anti-EGFR antibody include, without limitation, other agents that inhibit EGFR activity (including other antibodies or antigen-binding fragments thereof, peptide inhibitors, small molecule antagonists, etc.) and/or agents which do not directly bind EGFR but nonetheless interfere with, block or attenuate EGFR-mediated signaling.

In yet another aspect, the invention provides methods for inhibiting EGFR activity using an anti-EGFR antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of EGFR activity. The anti-EGFR antibodies or antibody fragments of the invention may function to block the interaction between EGFR and an EGFR binding partner (e.g., epidermal growth factor [EGF], transforming growth factor-alpha [TGF-α], etc.), or otherwise inhibit the signaling activity of EGFR.

The present invention also includes the use of an anti-EGFR antibody or antigen binding portion of an antibody of the invention in the manufacture of a medicament for the treatment of a disease or disorder related to or caused by EGFR activity in a patient.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "EGFR" and "EGFR fragment," as used herein refer to the human EGFR protein or fragment unless specified as being from a non-human species (e.g., "mouse EGFR," "mouse EGFR fragment," "monkey EGFR," "monkey EGFR fragment," etc.). The extracellular domain of human EGFR has the amino acid sequence shown in, e.g., amino acids 25 to 645 of SEQ ID NO:385.

As used herein, "an antibody that binds EGFR" or an "anti-EGFR antibody" includes antibodies, and antigen-binding fragments thereof, that bind a soluble fragment of an EGFR protein (e.g., a portion of the extracellular domain of EGFR) and/or cell surface-expressed EGFR. The expression "cell surface-expressed EGFR" means an EGFR protein or portion thereof that is/are expressed on the surface of a cell in vitro or in vivo, such that at least a portion of the EGFR protein (e.g., amino acids 25 to 645 of SEQ ID NO:385) is exposed to the extracellular side of the cell membrane and accessible to an antigen-binding portion of an antibody. Soluble EGFR molecules include, e.g., monomeric and dimeric EGFR constructs as described in Example 3 herein (i.e., "EGFR.mmh", SEQ ID NO:386, and "EGFR.mFc", SEQ ID NO:387, respectively), or constructs substantially similar thereto.

The term "antibody", as used herein, means any antigen-binding molecule or molecular complex comprising at least one complementarity determining region (CDR) that specifically binds to or interacts with a particular antigen (e.g., EGFR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-EGFR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. No. 5,500,362 and U.S. Pat. No. 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

A "neutralizing" or "blocking" antibody, as used herein, is intended to refer to an antibody whose binding to EGFR: (i) interferes with the interaction between EGFR or an EGFR fragment and an EGFR ligand (e.g., EGF, TGF-α, etc.), and/or (ii) results in inhibition of at least one biological function of EGFR. The inhibition caused by an EGFR neutralizing or blocking antibody need not be complete so long as it is detectable using an appropriate assay. Exemplary assays for detecting EGFR inhibition are described herein.

The anti-EGFR antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-EGFR antibodies comprising variants of any of the HCVR, LCVR, and/or CDR amino acid sequences disclosed herein having one or more conservative substitutions. For example, the present invention includes anti-EGFR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The present invention includes anti-EGFR antibodies and antigen-binding fragments thereof that bind monomeric or dimeric EGFR molecules with high affinity. For example, the present invention includes antibodies and antigen-binding fragments of antibodies that bind dimeric EGFR with a $K_D$ of less than about 20 pM as measured by surface plasmon resonance, e.g., using the assay format as defined in Example 3 herein. In certain embodiments, the antibodies or antigen-binding fragments of the present invention bind dimeric EGFR with a $K_D$ of less than about 15 pM, less than about 10 pM, less than about 8 pM, less than about 6 pM, less than about 4 pM, less than about 2 pM, or less than about 1 pM, as measured by surface plasmon resonance, e.g., using the assay format as defined in Example 3 herein. The present invention also includes anti-EGFR antibodies and antigen-binding fragments thereof that bind dimeric EGFR with a t½ of greater than about 200 minutes as measured by surface plasmon resonance, e.g., using the assay format as defined in Example 3 herein. In certain embodiments, the antibodies or antigen-binding fragments of the present invention bind dimeric EGFR with a t½ of greater than about 210 minutes, greater than about 220 minutes, greater than about 250 minutes, greater than about 260 minutes, greater than about 280 minutes, greater than about 300 minutes, greater than about 320 minutes, greater than about 340 minutes, greater than about 360 minutes, greater than about 380 minutes, greater than about 400 minutes, greater than about 450 minutes, greater than about 500 minutes, greater than about 550 minutes, greater than about 600 minutes, greater than about 650 minutes, greater than about 800 minutes, greater than about 1000 minutes, or more, as measured by surface plasmon resonance, e.g., using the assay format as defined in Example 3 herein.

The present invention also includes anti-EGFR antibodies and antigen-binding fragments thereof that inhibit the growth of EGFR-expressing tumor cells. For example, the present invention includes anti-EGFR antibodies and antigen-binding fragments thereof that inhibit the growth of tumor cells that express high levels of EGFR on their surface (e.g., A431 epidermoid carcinoma cells), with an $IC_{50}$ (i.e., the concentration resulting in 50% maximal growth inhibition) of less than about 200 pM. $IC_{50}$ values can be determined using the cell growth inhibition assay exemplified in Example 4 herein, or a substantially similar assay. According to certain embodiments of the present invention the anti-EGFR antibodies or antigen-binding fragments thereof are able to inhibit the growth of A431 cells in vitro with an $IC_{50}$ of less than about 180 pM, less than about 160 pM, less than about 140 pM, less than about 120 pM, less than about 100 pM, less than about 80 pM, less than about 60 pM, less than about 40 pM, less than about 20 pM, less than about 10 pM, less than about 5 pM, or less than about 2 pM, as determined using the cell growth inhibition assay exemplified in Example 4 herein, or a substantially similar assay.

The present invention also includes anti-EGFR antibodies and antigen-binding fragments thereof that induce antibody-dependent cell-mediated cytotoxicity (ADCC) of cells that express EGFR. Assays for measuring ADCC are known in the art. An exemplary assay format is illustrated in Example 5 herein, in which anti-EGFR antibodies are added to a cellular mixture of peripheral blood mononuclear cells (PBMCs) and A431 epidermoid carcinoma cells (i.e., cells expressing high levels of EGFR). The extent of cell killing is assessed relative to the maximal cell lysis signal observed under conditions in which untreated cells were lysed by addition of digitonin; the extent of ADCC can thereby be expressed in terms of the percent of maximum cell killing. The present invention includes anti-EGFR antibodies that produce a maximum cell killing percentage of greater than about 25%, when tested in the ADCC assay format of Example 5, or a substantially similar assay. In certain embodiments, the antibodies or antigen-binding fragments of the present invention induce ADCC with a maximum cell killing percentage of about 30%, about 35%, about 40%, about 45%, about 50%, about 55%, about 60%, about 65%, about 70%, about 75%, or more, as measured in the ADCC assay format of Example 5 or a substantially similar assay.

The present invention also includes anti-EGFR antibodies and antigen-binding fragments thereof that inhibit tumor growth in vitro or in vivo. In certain circumstances, the antibodies or antigen-binding fragments of the present invention cause tumor regression or shrinkage. The present invention includes anti-EGFR antibodies and antigen-binding fragments thereof that inhibit the growth of human tumor xenografts in immunocompromised mice. For example, as illustrated in Example 6 herein, the exemplary anti-EGFR antibody H1H141P significantly inhibited the growth of head and neck squamous cell carcinoma cells (e.g., FaDu tumor cells), pancreatic tumor cells (BxPC3), and lung tumor cells (Calu3 and NCI-H358), in mouse xenografts models. The invention includes antibodies and antigen-binding fragments thereof that inhibit tumor cell growth in tumor-bearing mice by greater than about 50% (e.g., about 55%, about 60%, about 65%, about 70%, about 75%, about 80%, about 85%, about 90%, about 95%, or more) as compared to hFc-control-treated tumor-bearing mice.

The present invention also includes anti-EGFR antibodies and antigen binding fragments thereof that induce internalization of cell surface expressed EGFR.

Epitope Mapping and Related Technologies

The present invention includes anti-EGFR antibodies which interact with one or more amino acids found within the extracellular domain of human EGFR (e.g., within extracellular domain I, II, III, and/or IV). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the extracellular domain of EGFR. Alternatively, the epitope may consist of a plurality of non-contiguous amino acids (or amino acid sequences) located within the extracellular domain of EGFR.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-EGFR antibodies that bind to the same epitope as any of the specific exemplary antibodies described herein (e.g. H1M085N, H1M086N, H1M089N, H1M102N, H1M103N, H1M116N, H1H134P, H1H136P, H1H141P, H1H142P, H1H143P, H1H144P, H1H145P, H1H147P, H1H151P, H1H153P, H1H155P, H1H157P, H1H158P, H1H159P, H1H161P, H1H163P, H1H169P, H1H171P etc.). Likewise, the present invention also includes anti-EGFR antibodies that compete for binding to EGFR with any of the specific exemplary antibodies described herein (e.g. H1M085N, H1M086N, H1M089N, H1M102N, H1M103N, H1M116N, H1H134P, H1H136P, H1H141P, H1H142P, H1H143P, H1H144P, H1H145P, H1H147P, H1H151P, H1H153P, H1H155P, H1H157P, H1H158P, H1H159P, H1H161P, H1H163P, H1H169P, H1H171P etc.).

One can easily determine whether an antibody binds to the same epitope as, or competes for binding with, a reference anti-EGFR antibody by using routine methods known in the art. For example, to determine if a test antibody binds to the same epitope as a reference anti-EGFR antibody of the invention, the reference antibody is allowed to bind to an EGFR protein (e.g., a soluble portion of the EGFR extracellular domain or cell surface-expressed EGFR). Next, the ability of a test antibody to bind to the EGFR molecule is assessed. If the test antibody is able to bind to EGFR following saturation binding with the reference anti-EGFR antibody, it can be concluded that the test antibody binds to a different epitope than the reference anti-EGFR antibody. On the other hand, if the test antibody is not able to bind to the EGFR molecule following saturation binding with the reference anti-EGFR antibody, then the test antibody may bind to the same epitope as the epitope bound by the reference anti-EGFR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-EGFR antibody, the above-described binding methodology is performed in two orientations: In a first orientation, the reference antibody is allowed to bind to an EGFR protein (e.g., a soluble portion of the EGFR extracellular domain or cell surface-expressed EGFR) under saturating conditions followed by assessment of binding of the test antibody to the EGFR molecule. In a second orientation, the test antibody is allowed to bind to an EGFR molecule under saturating conditions followed by assessment of binding of the reference antibody to the EGFR molecule. If, in both orientations, only the first (saturating) antibody is capable of binding to the EGFR molecule, then it is concluded that the test antibody and the reference antibody compete for binding to EGFR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human EGFR.

Using VELOCIMMUNE™ technology or any other known method for generating monoclonal antibodies, high affinity chimeric antibodies to EGFR are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-EGFR antibodies and antibody fragments of the present invention encompass proteins having amino acid sequences that vary from those of the described antibodies but that retain the ability to bind human EGFR. Such variant antibodies and antibody fragments comprise one or more additions, deletions, or substitutions of amino acids when compared to parent sequence, but exhibit biological activity that is essentially equivalent to that of the described antibodies. Likewise, the anti-EGFR antibody-encoding DNA sequences of the present invention encompass sequences that comprise one or more additions, deletions, or substitutions of nucleotides when compared to the disclosed sequence, but that encode an anti-EGFR antibody or antibody fragment that is essentially bioequivalent to an anti-EGFR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-EGFR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-EGFR antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-EGFR antibodies bind to human EGFR but not to EGFR from other species. The present invention also includes anti-EGFR antibodies that bind to human EGFR and to EGFR from one or more non-human species. For example, the anti-EGFR antibodies of the invention may bind to human EGFR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee EGFR.

Immunoconjugates

The invention encompasses anti-EGFR monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-EGFR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human EGFR or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-EGFR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with EGFR activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-EGFR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by EGFR expression or activity, or treatable by blocking the interaction between EGFR and an EGFR ligand (e.g., EGF or TGF-α) or otherwise inhibiting EGFR activity and/or signaling, and/or promoting receptor internalization and/or decreasing cell surface receptor number. For example, the antibodies and antigen-binding fragments of the present invention are useful for the treatment of tumors that express high levels of EGFR. The antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer (e.g., EGFR-dependent non-small cell lung cancer), synovial sarcoma, thyroid cancer, or melanoma.

Combination Therapies and Formulations

The present invention includes therapeutic administration regimens which comprise administering an anti-EGFR antibody of the present invention in combination with at least one additional therapeutically active component. Non-limiting examples of such additional therapeutically active components include other EGFR antagonists (e.g., a second anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET antagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), etc. Other agents that may be beneficially administered in combination with the anti-EGFR antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention also includes therapeutic combinations comprising any of the anti-EGFR antibodies mentioned herein and an inhibitor of one or more of VEGF, Ang2, DLL4, ErbB2, ErbB3, ErbB4, EGFRvIII, cMet, IGF1R, B-raf, PDGFR-α, PDGFR-β, or any of the aforementioned cytokines, wherein the inhibitor is an aptamer, an antisense molecule, a ribozyme, an siRNA, a peptibody, a nanobody or an antibody fragment (e.g., Fab fragment; F(ab')₂ fragment; Fd fragment; Fv fragment; scFv; dAb fragment; or other engineered molecules, such as diabodies, triabodies, tetrabodies, minibodies and minimal recognition units). The anti-EGFR antibodies of the invention may also be administered and/or co-formulated in combination with antivirals, antibiotics, analgesics, corticosteroids and/or NSAIDs. The anti-EGFR antibodies of the invention may also be administered as part of a treatment regimen that also includes radiation treatment and/or conventional chemotherapy.

The additional therapeutically active component(s) may be administered just prior to, concurrent with, or shortly after the administration of an anti-EGFR antibody of the present invention; (for purposes of the present disclosure, such administration regimens are considered the administration of an anti-EGFR antibody "in combination with" an additional therapeutically active component). The present invention includes pharmaceutical compositions in which an anti-EGFR antibody of the present invention is co-formulated with one or more of the additional therapeutically active component(s) as described elsewhere herein.

The present invention also includes compositions and methods comprising a combination of a "degrading antibody" and a "ligand-blocking antibody." A "degrading antibody" means an anti-EGFR antibody that causes degradation of EGFR in cells without necessarily blocking ligand-receptor interactions. A non-limiting example of a degrading antibody of the present invention is the antibody designated H1H134P. A "ligand-blocking antibody" means an anti-EGFR antibody that blocks the interaction between EGFR and one or more of its ligands (e.g., EGF or TGF-α). A non-limiting example of a ligand-blocking antibody of the present invention is the antibody designated H1H141P. Another example of a ligand blocking antibody is cetuximab. The present inventors have conceived of combining a degrading antibody and a ligand-blocking antibody in order to synergistically or otherwise improve anti-tumor efficacy. Accordingly, the present invention includes pharmaceutical compositions comprising at least one degrading antibody and at least one ligand-blocking antibody. The present invention also includes therapeutic methods comprising administering to a subject a combination of a degrading antibody and a ligand-blocking antibody (either as separate administrations or as co-formulations).

Diagnostic Uses of the Antibodies

The anti-EGFR antibodies of the present invention may also be used to detect and/or measure EGFR, or EGFR-expressing cells in a sample, e.g., for diagnostic purposes. For example, an anti-EGFR antibody, or fragment thereof, may be used to diagnose a condition or disease characterized by aberrant expression (e.g., over-expression, under-expression, lack of expression, etc.) of EGFR. Exemplary diagnostic assays for EGFR may comprise, e.g., contacting a sample, obtained from a patient, with an anti-EGFR antibody of the invention, wherein the anti-EGFR antibody is labeled with a detectable label or reporter molecule. Alternatively, an unlabeled anti-EGFR antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure EGFR in a sample include enzyme-linked immunosorbent assay (ELISA), radioimmunoassay (RIA), and fluorescence-activated cell sorting (FACS).

Samples that can be used in EGFR diagnostic assays according to the present invention include any tissue or fluid sample obtainable from a patient which contains detectable quantities of EGFR protein, or fragments thereof, under normal or pathological conditions. Generally, levels of EGFR in a particular sample obtained from a healthy patient (e.g., a patient not afflicted with a disease or condition associated with abnormal EGFR levels or activity) will be measured to initially establish a baseline, or standard, level of EGFR. This baseline level of EGFR can then be compared against the levels of EGFR measured in samples obtained from individuals suspected of having a EGFR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to EGFR

An EGFR-expressing cell line was administered directly, with an adjuvant to stimulate the immune response, to a VELOCIMMUNE® mouse comprising DNA encoding human Immunoglobulin heavy and kappa light chain variable regions. The antibody immune response was monitored by a EGFR-specific immunoassay. When a desired immune response was achieved splenocytes were harvested and fused with mouse myeloma cells to preserve their viability and form hybridoma cell lines. The hybridoma cell lines were screened and selected to identify cell lines that produce EGFR-specific antibodies. Using this technique several anti-EGFR chimeric antibodies (i.e., antibodies possessing human variable domains and mouse constant domains) were obtained; exemplary antibodies generated in this manner were designated as follows: H1M085N, H1M086N, H1M089N, H1M102N, H1M103N, and H1M116N.

Anti-EGFR antibodies were also isolated directly from antigen-positive B cells without fusion to myeloma cells, as described in US 2007/0280945A1. Using this method, several fully human anti-EGFR antibodies (i.e., antibodies possessing human variable domains and human constant domains) were obtained; exemplary antibodies generated in this manner were designated as follows: H1H134P, H1H136P, H1H141P, H1H142P, H1H143P, H1H144P, H1H145P, H1H147P, H1H151P, H1H153P, H1H155P, H1H157P, H1H158P, H1H159P, H1H161P, H1H163P, H1H169P, and H1H171P.

Certain biological properties of the exemplary anti-EGFR antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected anti-EGFR antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 085N | 2 | 4 | 6 | 8 | 10 | 12 | 14 | 16 |
| 086N | 18 | 20 | 22 | 24 | 26 | 28 | 30 | 32 |
| 089N | 34 | 36 | 38 | 40 | 42 | 44 | 46 | 48 |
| 102N | 50 | 52 | 54 | 56 | 58 | 60 | 62 | 64 |
| 103N | 66 | 68 | 70 | 72 | 74 | 76 | 78 | 80 |
| 116N | 82 | 84 | 86 | 88 | 90 | 92 | 94 | 96 |
| 134P | 98 | 100 | 102 | 104 | 106 | 108 | 110 | 112 |

TABLE 1-continued

| Antibody Designation | HCVR | HCDR1 | HCDR2 | HCDR3 | LCVR | LCDR1 | LCDR2 | LCDR3 |
|---|---|---|---|---|---|---|---|---|
| 136P | 114 | 116 | 118 | 120 | 122 | 124 | 126 | 128 |
| 141P | 130 | 132 | 134 | 136 | 138 | 140 | 142 | 144 |
| 142P | 146 | 148 | 150 | 152 | 154 | 156 | 158 | 160 |
| 143P | 162 | 164 | 166 | 168 | 170 | 172 | 174 | 176 |
| 144P | 178 | 180 | 182 | 184 | 186 | 188 | 190 | 192 |
| 145P | 194 | 196 | 198 | 200 | 202 | 204 | 206 | 208 |
| 147P | 210 | 212 | 214 | 216 | 218 | 220 | 222 | 224 |
| 151P | 226 | 228 | 230 | 232 | 234 | 236 | 238 | 240 |
| 153P | 242 | 244 | 246 | 248 | 250 | 252 | 254 | 256 |
| 155P | 258 | 260 | 262 | 264 | 266 | 268 | 270 | 272 |
| 157P | 274 | 276 | 278 | 280 | 282 | 284 | 286 | 288 |
| 158P | 290 | 292 | 294 | 296 | 298 | 300 | 302 | 304 |
| 159P | 306 | 308 | 310 | 312 | 314 | 316 | 318 | 320 |
| 161P | 322 | 324 | 326 | 328 | 330 | 332 | 334 | 336 |
| 163P | 338 | 340 | 342 | 344 | 346 | 348 | 350 | 352 |
| 169P | 354 | 356 | 358 | 360 | 362 | 364 | 366 | 368 |
| 171P | 370 | 372 | 374 | 376 | 378 | 380 | 382 | 384 |

Antibodies are typically referred to herein according to the following nomenclature: Fc prefix (e.g. "H1H" or "H1M"), followed by a numerical identifier (e.g. "085" or "134" as shown in Table 1), followed by a "P" or "N" suffix. Thus, according to this nomenclature, an antibody may be referred to herein as, e.g., "H1M085N" or "H1H134P", etc. The H1H and H1M prefixes on the antibody designations used herein indicate the particular Fc region of the antibody. For example, an "H1M" antibody has a mouse IgG1 Fc, whereas an "H1H" antibody has a human IgG1 Fc. As will be appreciated by a person of ordinary skill in the art, an H1M antibody can be converted to an H1H antibody, and vice versa, but in any event, the variable domains (including the CDRs)—which are indicated by the numerical identifiers shown in Table 1—will remain the same.

Control Constructs Used in the Following Examples

Various control constructs (anti-EGFR antibodies) were included in the following experiments for comparative purposes. The control constructs are designated as follows: Control I: a chimeric anti-EGFR antibody with heavy and light chain variable sequences of "mAb 225" as set forth in U.S. Pat. No. 7,060,808; and Control II: a commercially available fully human monoclonal anti-EGFR antibody designated as ABX-EGF, also known as Panitumumab or Vectibix®.

Example 3. Antibody Binding to Human EGFR as Determined by Surface Plasmon Resonance Equilibrium dissociation constants ($K_D$ values) for antigen binding to selected purified anti-human EGFR monoclonal antibodies were determined using a real-time surface plasmon resonance biosensor (Biacore T100) assay at 37° C. The Biacore sensor surface was derivatized with monoclonal mouse anti-human Fc antibody (GE Biosciences) to capture anti-EGFR monoclonal antibodies, expressed in the human IgG1 Fc format (antibody prefix H1H). Different concentrations of human monomeric (EGFR.mmh; SEQ ID NO:386) and dimeric (EGFR.mFc; SEQ ID NO:387) proteins were injected over the anti-EGFR monoclonal antibody captured surface at a flow rate of 50 μl/min. Antibody-antigen association was monitored for 4-5 minutes while dissociation of antigen from the captured monoclonal antibody surface was monitored for 10 min. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=$\ln2/(60*k_d)$. Kinetic binding parameters for different anti-EGFR monoclonal antibodies are shown in Table 2.

TABLE 2

Binding Characteristics of Anti-EGFR Antibodies to Monomeric and Dimeric EGFR

| Antibody | Analyte | ka (Ms$^{-1}$) | kd (s$^{-1}$) | K$_D$ (Molar) | t$_{1/2}$ (min) |
|---|---|---|---|---|---|
| H1H0085N | EGFR.mmh | 1.19E+05 | 1.85E−03 | 1.55E−08 | 6 |
|  | EGFR.mFc | 3.36E+05 | 4.05E−05 | 1.20E−10 | 286 |
| H1H086N | EGFR.mmh | 5.40E+05 | 7.08E−04 | 1.31E−09 | 16 |
|  | EGFR.mFc | 1.90E+06 | 1.13E−05 | 5.98E−12 | 1018 |
| H1H089N | EGFR.mmh | 3.13E+05 | 6.83E−03 | 2.18E−08 | 2 |
|  | EGFR.mFc | 1.49E+06 | 4.49E−05 | 3.01E−11 | 257 |
| H1H102N | EGFR.mmh | 1.66E+05 | 9.43E−04 | 5.67E−09 | 12 |
|  | EGFR.mFc | 8.63E+05 | 5.62E−05 | 6.51E−11 | 206 |
| H1H103N | EGFR.mmh | 1.00E+05 | 1.39E−03 | 1.39E−08 | 8 |
|  | EGFR.mFc | 3.83E+05 | 4.19E−05 | 1.09E−10 | 276 |
| H1H116N | EGFR.mmh | 5.39E+05 | 2.84E−03 | 5.27E−09 | 4 |
|  | EGFR.mFc | 1.55E+06 | 3.16E−05 | 2.03E−11 | 366 |
| H1H134P | EGFR.mmh | 9.30E+05 | 7.89E−04 | 8.48E−10 | 15 |
|  | EGFR.mFc | 3.09E+06 | 2.47E−05 | 7.99E−12 | 468 |
| H1H136P | EGFR.mmh | NB | NB | NB | NB |
|  | EGFR.mFc | NB | NB | NB | NB |
| H1H141P | EGFR.mmh | 3.96E+05 | 4.05E−04 | 1.02E−09 | 29 |
|  | EGFR.mFc | 9.03E+05 | 7.51E−06 | 8.31E−12 | 1539 |
| H1H142P | EGFR.mmh | 1.58E+05 | 6.89E−04 | 4.35E−09 | 17 |
|  | EGFR.mFc | 3.61E+05 | 1.20E−05 | 3.32E−11 | 965 |
| H1H143P | EGFR.mmh | 1.27E+05 | 7.27E−04 | 5.71E−09 | 16 |
|  | EGFR.mFc | 3.81E+05 | 1.35E−05 | 3.54E−11 | 856 |
| H1H144P | EGFR.mmh | 1.84E+05 | 9.67E−04 | 5.25E−09 | 12 |
|  | EGFR.mFc | 8.94E+05 | 1.94E−05 | 2.17E−11 | 596 |
| H1H145P | EGFR.mmh | 1.37E+05 | 1.95E−04 | 1.43E−09 | 59 |
|  | EGFR.mFc | 2.52E+05 | 5.86E−06 | 2.32E−11 | 197 |
| H1H147P | EGFR.mmh | 6.54E+04 | 3.76E−04 | 5.76E−09 | 31 |
|  | EGFR.mFc | 1.90E+05 | 1.26E−05 | 6.64E−11 | 914 |
| H1H151P | EGFR.mmh | 1.34E+05 | 1.13E−03 | 8.40E−09 | 10 |
|  | EGFR.mFc | 1.34E+05 | 1.13E−03 | 8.40E−09 | 10 |
| H1H153P | EGFR.mmh | 7.61E+04 | 2.35E−04 | 3.09E−09 | 49 |
|  | EGFR.mFc | 2.34E+05 | 8.23E−06 | 3.51E−11 | 1403 |
| H1H155P | EGFR.mmh | 1.76E+05 | 1.69E−04 | 9.62E−10 | 68 |
|  | EGFR.mFc | 3.29E+05 | 1.06E−04 | 3.21E−10 | 109 |
| H1H157P | EGFR.mmh | NB | NB | NB | NB |
|  | EGFR.mFc | NB | NB | NB | NB |
| H1H158P | EGFR.mmh | 1.31E+05 | 7.73E−04 | 5.90E−09 | 15 |
|  | EGFR.mFc | 4.08E+05 | 9.84E−06 | 2.41E−11 | 1174 |
| H1H159P | EGFR.mmh | 4.76E+05 | 3.25E−04 | 6.82E−10 | 36 |
|  | EGFR.mFc | 1.64E+06 | 5.63E−06 | 3.44E−12 | 2051 |
| H1H161P | EGFR.mmh | 4.89E+05 | 3.21E−04 | 6.55E−10 | 36 |
|  | EGFR.mFc | 1.73E+06 | 2.76E−06 | 1.59E−12 | 4187 |
| H1H163P | EGFR.mmh | 5.11E+05 | 4.26E−04 | 8.34E−10 | 27 |
|  | EGFR.mFc | 1.81E+06 | 2.12E−06 | 1.17E−12 | 5447 |

TABLE 2-continued

Binding Characteristics of Anti-EGFR Antibodies to Monomeric and Dimeric EGFR

| Antibody | Analyte | ka (Ms$^{-1}$) | kd (s$^{-1}$) | K$_D$ (Molar) | t$_{1/2}$ (min) |
|---|---|---|---|---|---|
| H1H169P | EGFR.mmh | 6.65E+05 | 8.69E−04 | 1.31E−09 | 13 |
| | EGFR.mFc | 2.29E+06 | 1.69E−05 | 7.36E−12 | 684 |
| H1H171P | EGFR.mmh | 7.94E+04 | 1.13E−03 | 1.42E−08 | 10 |
| | EGFR.mFc | 3.39E+05 | 3.48E−05 | 1.03E−10 | 332 |
| Control I | EGFR.mmh | 1.58E+06 | 7.38E−03 | 4.68E−09 | 2 |
| | EGFR.mFc | 3.55E+06 | 1.08E−04 | 3.03E−11 | 107 |
| Control II | EGFR.mmh | 7.12E+05 | 7.62E−04 | 1.07E−09 | 15 |
| | EGFR.mFc | 1.38E+06 | 5.82E−05 | 4.23E−11 | 198 |

As shown in Table 2, several of the anti-EGFR antibodies of the present invention exhibited superior binding properties as compared to the control antibodies. For example, certain anti-EGFR antibodies of the present invention exhibited K$_D$ values less than 10 pM and t½ values greater than 400 minutes, when tested for binding to dimeric EGFR ("EGFR.mFc") in the surface plasmon resonance assay described above; e.g., H1H086N (5.98 pM/1018 min), H1H134P (7.99 pM/468 min), H1H141P (8.31 pM/1539 min), H1H159P (3.44 pM/2059 min), H1H161P (1.59 pM/4187 min), and H1H169P (7.36 pM/684 min). By contrast, Control I exhibited a K$_D$ of 30.3 pM and a t½ of 107 min, and Control II exhibited a K$_D$ of 42.3 pM and a t½ of 198 min when tested for binding to dimeric EGFR under identical experimental conditions.

Example 4. Inhibition of Cell Growth by Anti-EGFR Antibodies

Anti-EGFR antibodies were tested for their ability to inhibit the growth of A431 epidermoid carcinoma cells in vitro. A431 cells have an amplification of the EGFR gene and exhibit a strong dependence on EGFR signaling for growth. A431 cells were seeded at a density of 5.0×10³ cells per well in 96-well plates and incubated in DMEM medium containing 0.5% BSA and 1% penicillin/streptomycin/glutamine. EGFR-specific mAbs were added to cells in 1:3 serial dilutions starting at 60 nM. After 7 days viable cells were quantified by staining with Alamar Blue (Invitrogen) and measuring fluorescence with a Flexstation III spectrophotometer. Absorbance values were plotted using a four-parameter logistic equation over the 12-point dilution series (GraphPad Prism). Results are summarized in Table 3.

TABLE 3

Relative Inhibition of A431 Cell Proliferation by Anti-EGFR Antibodies

| Antibody | IC$_{50}$ of A431 Proliferation (Molar) |
|---|---|
| H1H0085N | 1.645E−09 |
| H1H086N | 5.459E−10 |
| H1H089N | 2.305E−09 |
| H1H102N | 2.883E−10 |
| H1H103N | 3.89E−09 |
| H1H116N | 2.24E−10 |
| H1H134P | 1.844E−09 |
| H1H136P | No Inhibition |
| H1H141P | 1.405E−10 |
| H1H142P | 5.474E−10 |
| H1H143P | 9.968E−11 |
| H1H144P | 1.393E−11 |
| H1H145P | No Inhibition |
| H1H147P | 9.769E−11 |
| H1H151P | 2.77E−10 |
| H1H153P | No Inhibition |
| H1H155P | No Inhibition |
| H1H157P | No Inhibition |
| H1H158P | No Inhibition |
| H1H159P | No Inhibition |
| H1H161P | No Inhibition |
| H1H163P | No Inhibition |
| H1H169P | No Inhibition |
| H1H171P | No Inhibition |
| Control I | 3.346E−10 |

As shown in Table 3, the tested antibodies exhibited a broad range of IC$_{50}$ values with some antibodies possessing little to no blocking activity while others displayed IC$_{50}$ values lower than the reference Control I antibody. For example, anti-EGFR antibodies H1H141P, H1H143P, H1H144P and H1H147P all exhibited IC$_{50}$ values less than 200 pM, whereas, the Control I antibody exhibited an IC$_{50}$ value of greater than 334 pM.

Example 5. Induction of ADCC on A431 Cells by Anti-EGFR Antibodies

Antibody dependent cell-mediated cytotoxicity (ADCC) is a cellular process which occurs when Fc receptors on natural killer cells are activated to induce the release of cell-lysing enzymes against target cells. The ability of anti-EGFR antibodies to induce ADCC in vitro was assessed by using peripheral blood mononuclear cells (PBMC) as effector, or primary "killer" cells, against A431 target cells that endogenously over-express EGFR.

Briefly, anti-EGFR antibodies over a broad concentration range (40 nM-0 nM; 1:3 dilutions) were added to a cellular mixture of PBMC and A431 cells (30:1 ratio) in 96-well plates. The plates were incubated for 4 hours at 37° C., 5% CO$_2$, equilibrated to room temperature for 10 minutes and CytoTox-Glo reagent was added to the wells. Untreated cells in control wells were lysed by addition of digitonin to determine maximal cell lysis signal. The plates were incubated briefly at room temperature and luminescence was measured from each well using a plate reader.

Cytotoxic response was calculated by subtracting the signal for A431 cells incubated with PBMC without the addition of anti-EGFR antibodies (background) from the signal generated from target cells mixed with PBMC in the presence of anti-EGFR mAbs. The percentage of cytotoxicity was calculated by dividing the cytotoxic response of cells against background by the maximal cytotoxic response obtained from cell lysis via digitonin. Data was analyzed by a four-parameter logistical equation with a sigmoidal dose-response curve (GraphPad Prism). Results are summarized in Table 4. (NA=no activity).

TABLE 4

ADCC Activity of Selected Anti-EGFR Antibodies

| Antibody | EC$_{50}$ (Molar) | Maximum Cell Killing (%) |
|---|---|---|
| H1H0085N | 3.70E−13 | 35 |
| H1H086N | 2.91E−13 | 25 |
| H1H089N | 5.83E−12 | 53 |
| H1H102N | 4.39E−13 | 48 |
| H1H103N | 7.25E−13 | 17 |
| H1H116N | 2.51E−13 | 29 |
| H1H134P | 4.61E−11 | 33 |

TABLE 4-continued

ADCC Activity of Selected Anti-EGFR Antibodies

| Antibody | EC$_{50}$ (Molar) | Maximum Cell Killing (%) |
|---|---|---|
| H1H136P | 1.49E−09 | 27 |
| H1H141P | 2.78E−12 | 41 |
| H1H142P | 1.19E−12 | 34 |
| H1H143P | NA | 13 |
| H1H144P | 4.57E−11 | 43 |
| H1H145P | NA | 0 |
| H1H147P | NA | 13 |
| H1H151P | 5.48E−09 | 68 |
| H1H153P | 2.65E−11 | 31 |
| H1H155P | 1.67E−11 | 30 |
| H1H157P | 2.27E−13 | 36 |
| H1H158P | 2.32E−12 | 28 |
| H1H159P | 2.69E−09 | 60 |
| H1H161P | 9.80E−12 | 38 |
| H1H163P | 2.96E−10 | 48 |
| H1H169P | 4.81E−09 | 27 |
| H1H171P | 8.94E−13 | 27 |
| Control I | 1.86E−12 | 24 |

As shown in Table 4, several anti-EGFR mAbs induced ADCC on A431 cells co-incubated with PBMC effector cells. Additionally, several anti-EGFR mAbs demonstrate a high maximal cell killing percentage comparable to the control antibody (Control I). For example, anti-EGFR antibodies H1H089N, H1H102N, H1H141P, H1H144P, H1H151P, H1H159P and H1H163P each exhibited greater than 40% maximum cell killing in the ADCC assay, whereas the Control I antibody exhibited less than 25% maximum cell killing in this assay.

Example 6. Inhibition of Tumor Growth by an Anti-EGFR Antibody

The anti-EGFR antibody H1H141P was tested for its ability to inhibit the growth human tumor xenografts in immunocompromised mice. Briefly, 2×10^6 FaDu head and neck squamous cell carcinoma cells were implanted subcutaneously into the flank of C.B.-17 SCID mice. After tumors reached an average size of approximately 200 mm$^3$ mice were randomized into groups for treatment (N=6 mice per group) and injected twice per week subcutaneously with either human Fc control protein (12.5 mg/kg; SEQ ID NO:388) or with H1H141P (10 mg/kg). Mice were treated for 15 days.

Tumor volumes were measured twice per week throughout the experiment and tumor weights were determined upon excision at the conclusion of the experiment. The average tumor growth (the average change in tumor volume from the start of treatment through the end of the experiment) and the average tumor weights were determined for each group. Results are summarized in Table 5.

TABLE 5

Inhibition of FaDu Tumor Growth in SCID Mice

| Antibody (mg/kg) | Tumor Growth (mm$^3$) from start of treatment (mean ± SD) | % Decrease in Tumor Growth vs Control | Tumor Weight (g) (mean ± SD) | % Decrease in Tumor Weight vs Control |
|---|---|---|---|---|
| hFc Control (12.5) | 1099 ± 186 | — | 0.993 ± 0.176 | — |
| H1H141P (10) | 55 ± 115 | 95 | 0.215 ± 0.120 | 78 |

In a similar experiment, the effect of H1H141P on the growth of BxPC3 pancreatic tumor xenografts was determined, as summarized in Table 6.

TABLE 6

Inhibition of BxPC3 Tumor Growth in SCID Mice

| Antibody (mg/kg) | Tumor Growth (mm$^3$) from start of treatment (mean ± SD) | % Decrease in Tumor Growth vs Control | Tumor Weight (g) (mean ± SD) | % Decrease in Tumor Weight vs Control |
|---|---|---|---|---|
| hFc Control (25) | 706 ± 277 | — | 0.926 ± 0.412 | — |
| H1H141P (12.5) | 97 ± 59 | 86 | 0.275 ± 0.098 | 70 |

In a similar experiment, the effect of H1H141P on the growth of Calu3 lung tumor xenografts was determined, as summarized in Table 7.

TABLE 7

Inhibition of Calu3 Tumor Growth in SCID Mice

| Antibody (mg/kg) | Tumor Growth (mm$^3$) from start of treatment (mean ± SD) | % Decrease in Tumor Growth vs Control | Tumor Weight (g) (mean ± SD) | % Decrease in Tumor Weight vs Control |
|---|---|---|---|---|
| hFc Control (25) | 656 ± 202 | — | 0.884 ± 0.275 | — |
| H1H141P (25) | 335 ± 58 | 49 | 0.582 ± 0.097 | 34 |

In a similar experiment, the effect of H1H141P on the growth of NCI-H358 lung tumor xenografts was determined, as summarized in Table 8.

TABLE 8

Inhibition of NCI-H358 Tumor Growth in SCID Mice

| Antibody (mg/kg) | Tumor Growth (mm³) from start of treatment (mean ± SD) | % Decrease in Tumor Growth vs Control |
|---|---|---|
| hFc Control (25) | 329 ± 170 | — |
| H1H141P (12.5) | (−14) ± 47 | 104 |

In a similar experiment, the effect of H1H141P on the growth of A431 epidermoid carcinoma xenografts was determined, as summarized in Table 9.

TABLE 9

Inhibition of A431 Tumor Growth in SCID Mice

| Antibody (mg/kg) | Tumor Growth (mm³) from start of treatment (mean ± SD) | % Decrease in Tumor Growth vs Control |
|---|---|---|
| hFc Control (25) | 134 ± 173 | — |
| H1H141P (12.5) | 62 ± 49 | 95 |
| H1H141P (25) | 45 ± 60 | 97 |

Collectively, these findings indicate that H1H141P as a monotherapy can inhibit the growth of multiple human tumor xenografts, representing several different tumor types.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for inhibiting tumor growth, the method comprising administering to a subject afflicted with a tumor a pharmaceutical composition comprising an antibody or antigen-binding fragment thereof that specifically binds human epidermal growth factor receptor (hEGFR), wherein the antibody or antigen-binding fragment thereof comprises: (a) the complementarity determining regions (CDRs) of a heavy chain variable region (HCVR) comprising the amino acid sequence of SEQ ID NO:130, and (b) the CDRs of a light chain variable region (LCVR) comprising the amino acid sequence of SEQ ID NO:138.

2. The method of claim 1, wherein the antibody or antigen-binding fragment thereof comprises the heavy and light chain CDRs of a HCVR/LCVR amino acid sequence pair having SEQ ID NOs: 130/138.

3. The method of claim 2, wherein the antibody or antigen-binding fragment thereof comprises HCDR1, HCDR2, HCDR3, LCDR1, LCDR2, and LCDR3 domains, respectively, having SEQ ID NOs: 132, 134, 136, 140, 142, and 144.

4. The method of claim 1, wherein the tumor is selected from the group consisting of a renal tumor, a pancreatic tumor, a head and neck tumor, a breast tumor, a prostate tumor, a colon tumor, a gastric tumor, an ovarian tumor, a lung tumor, and a skin tumor.

5. The method of claim 1, further comprising administering to the subject a second therapeutic agent.

6. The method of claim 5, wherein the second therapeutic agent is an antibody or antigen-binding fragment thereof that specifically binds HER2, ErbB3, ErbB4, cMet, IGF1R, Ang2, PDGFR-α or PDGFR-β.

7. The method of claim 5, wherein the second therapeutic agent is a VEGF antagonist.

8. The method of claim 7, wherein the VEGF antagonist is a VEGF-Trap.

9. The method of claim 7, wherein the VEGF antagonist is an anti-VEGF antibody.

10. The method of claim 9, wherein the anti-VEGF antibody is bevacizumab.

11. The method of claim 7, wherein the VEGF antagonist is a small molecule kinase inhibitor of VEGF receptor.

12. The method of claim 11, wherein the small molecule kinase inhibitor of VEGF receptor is sunitinib, sorafenib or pazopanib.

13. The method of claim 1, wherein the antibody or antigen-binding fragment thereof is administered as part of a treatment regimen that also includes radiation treatment and/or conventional chemotherapy.

* * * * *

```
                        SEQUENCE LISTING

<160> NUMBER OF SEQ ID NOS: 388

<210> SEQ ID NO 1
<211> LENGTH: 360
<212> TYPE: DNA
<213> ORGANISM: Artificial Sequence
<220> FEATURE:
<223> OTHER INFORMATION: Synthetic

<400> SEQUENCE: 1
gaagtgcagc tggtggagtc tgggggaggc ttggtgcagc ctggcaggtc cctgagactc      60
tcctgtgcag cctctggatt cacctttgat gattatgcca tgcactgggt ccggcaagct     120
ccagggaagg gcctggagtg ggtctcaggt attaattgga atagtgataa aatagcctat     180
gcggactctg tgaagggccg attcaccatc tccagagaca acgccgagaa ctccctgttt     240
ctgcaaatga atagtctgag acctgaggac acggccttgt attactgtgt aaaaagggc      300 gatttttgga ctgagtatta tgactattgg ggccagggaa ccctggtcac cgtctcctca     360

<210> SEQ ID NO 2
<211> LENGTH: 120
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Asn Trp Asn Ser Asp Lys Ile Ala Tyr Ala Asp Ser Val
        50                  55                  60

Lys Gly Arg Phe Thr Ile Ser Arg Asp Asn Ala Glu Asn Ser Leu Phe
 65                 70                  75                  80

Leu Gln Met Asn Ser Leu Arg Pro Glu Asp Thr Ala Leu Tyr Tyr Cys
                85                  90                  95
```

Val Lys Arg Gly Asp Phe Trp Thr Glu Tyr Tyr Asp Tyr Trp Gly Gln
            100                 105                 110

Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct ttgatgatta tgcc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asp Asp Tyr Ala
 1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attaattgga atagtgataa aata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Asn Trp Asn Ser Asp Lys Ile
 1               5

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gtaaaaaggg gcgattttg gactgagtat tatgactat                           39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Val Lys Arg Gly Asp Phe Trp Thr Glu Tyr Tyr Asp Tyr

<210> SEQ ID NO 9
<211> LENGTH: 336
<212> TYPE: DNA
<213> ORGANISM: Artificial Sequence
<220> FEATURE:
<223> OTHER INFORMATION: Synthetic

<400> SEQUENCE: 9

```
gatattgtga tgactcagtc tccactctcc ctgcccgtca cccctggaga gccggcctcc    60
atctcctgca ggtctagtca gagcctcctt catagtaatg gatacaacta tttagattgg   120
tacctgcaga agccagggca gtctccacac ctcctgatct atttggtttc tactcgggcc   180
tccggggtcc ctgacaggtt cagtggcagt ggatcaggca cagattttac actgaaaatc   240
agcagagtgg aggctgagga tgttggagtt tattactgca tacaggctct acaaactccg   300
tggacgttcg gccaagggac caaggtggaa atcaaa                             336
```

<210> SEQ ID NO 10
<211> LENGTH: 112
<212> TYPE: PRT
<213> ORGANISM: Artificial Sequence
<220> FEATURE:
<223> OTHER INFORMATION: Synthetic

<400> SEQUENCE: 10

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Leu Gln Lys Pro Gly Gln Ser
        35                  40                  45
Pro His Leu Leu Ile Tyr Leu Val Ser Thr Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ile Gln Ala
                85                  90                  95
Leu Gln Thr Pro Trp Thr Phe Gly Gln Gly Thr Lys Val Glu Ile Lys
            100                 105                 110
```

<210> SEQ ID NO 11
<211> LENGTH: 33
<212> TYPE: DNA
<213> ORGANISM: Artificial Sequence
<220> FEATURE:
<223> OTHER INFORMATION: Synthetic

<400> SEQUENCE: 11

```
cagagcctcc ttcatagtaa tggatacaac tat                                 33
```

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

```
Gln Ser Leu Leu His Ser Asn Gly Tyr Asn Tyr
1               5                   10
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ttggtttct                                                                 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Leu Val Ser
 1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atacaggctc tacaaactcc gtggacg                                            27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ile Gln Ala Leu Gln Thr Pro Trp Thr
 1               5

<210> SEQ ID NO 17
<211> LENGTH: 360
<212> TYPE: DNA
<213> ORGANISM: Artificial Sequence
<220> FEATURE:
<223> OTHER INFORMATION: Synthetic

<400> SEQUENCE: 17
gaagtgcagt tggtggagtc tgggggaggc ttggtgcagc ctggcaggtc cctgagactc         60
tcctgtgcag cctctggatt cacctttgat gattatgcca tgcactgggt ccggcaagct        120
ccaggaaagg gcctggagtg gtctcaggt attaattgga atagtgataa gatagcctat        180
gcggactctg tgaagggccg attcaccatc tccagagaca cgccgagaa ctccctgttt        240 ctgcaaatga atagtctgag acctgaggac acggccttgt attactgtgt aaaaaggggc        300 gattttttgga ctgattatta tgactattgg ggccagggaa ccctggtcac cgtctcctca        360

<210> SEQ ID NO 18
<211> LENGTH: 120
<212> TYPE: PRT
<213> ORGANISM: Artificial Sequence
<220> FEATURE:

<223> OTHER INFORMATION: Synthetic

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Asp Lys Ile Ala Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Ser Leu Arg Pro Glu Asp Thr Ala Leu Tyr Tyr Cys
                85                  90                  95

Val Lys Arg Gly Asp Phe Trp Thr Asp Tyr Tyr Asp Tyr Trp Gly Gln
            100                 105                 110

Gly Thr Leu Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct ttgatgatta tgcc                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Asp Asp Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attaattgga atagtgataa gata                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Asn Trp Asn Ser Asp Lys Ile
1               5

-continued

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
gtaaaaaggg gcgattttg gactgattat tatgactat                                39

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Val Lys Arg Gly Asp Phe Trp Thr Asp Tyr Tyr Asp Tyr
 1               5                  10

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25
gatattgtga tgactcagtc tccactctcc ctgcccgtca cccctggaga gccggcctcc        60
atctcctgca ggtctagtca gagcctcctt catagtaatg gatacaacta tttggattgg      120
tacctgcaga agccagggca gtctccacac ctcctgatct atttggtttc tactcgggcc      180
tccggggtcc ctgacaggtt cagtggcagt ggatcaggca cagattttac actgaaaatc      240
agcagagtgg aggctgagga tgttggagtt tattactgca tgcaggctct acaaactccg      300
tggacgttcg gccaagggac caaggtggaa atcaaa                                336

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro His Leu Leu Ile Tyr Leu Val Ser Thr Arg Ala Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 27

```
<211> LENGTH: 33
<212> TYPE: DNA
<213> ORGANISM: Artificial Sequence
<220> FEATURE:
<223> OTHER INFORMATION: Synthetic

<400> SEQUENCE: 27
cagagcctcc ttcatagtaa tggatacaac tat                               33

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Gln Ser Leu Leu His Ser Asn Gly Tyr Asn Tyr
 1               5                  10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ttggtttct                                                          9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Leu Val Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
atgcaggctc tacaaactcc gtggacg                                      27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Met Gln Ala Leu Gln Thr Pro Trp Thr
 1               5

<210> SEQ ID NO 33
<211> LENGTH: 360
<212> TYPE: DNA
<213> ORGANISM: Artificial Sequence
<220> FEATURE:
```

<223> OTHER INFORMATION: Synthetic

<400> SEQUENCE: 33

```
gaagtgcagc tggtggagtc tgggggaggc ttggtgcagc ctggcaggtc cctgagactc      60
tcctgtgcag cctctggatt cacctttgat gattatgcca tgcactgggt ccggcaagct     120
ccagggaagg gcctggagtg ggtctcaggt attaattgga atagtgataa aatagcctat     180
gcggactctg tgaagggccg attcaccatc tccagagaca acgccgagaa ctccctgttt     240
ctgcaaatga atagtctgag acctgaggac acggccttgt attactgtgt aaaaagggc     300
gatttttgga ctgattatta tgactattgg ggccagggaa ccctggtcac cgtctcctct     360
```

<210> SEQ ID NO 34
<211> LENGTH: 120
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Asp Lys Ile Ala Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Ser Leu Arg Pro Glu Asp Thr Ala Leu Tyr Tyr Cys
                85                  90                  95

Val Lys Arg Gly Asp Phe Trp Thr Asp Tyr Tyr Asp Tyr Trp Gly Gln
            100                 105                 110

Gly Thr Leu Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35

```
ggattcacct ttgatgatta tgcc                                              24
```

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Asp Asp Tyr Ala
1               5

<210> SEQ ID NO 37
<211> LENGTH: 24
<212> TYPE: DNA

```
<213> ORGANISM: Artificial Sequence
<220> FEATURE:
<223> OTHER INFORMATION: Synthetic

<400> SEQUENCE: 37
attaattgga atagtgataa aata                                              24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Asn Trp Asn Ser Asp Lys Ile
 1               5

<210> SEQ ID NO 39
<211> LENGTH: 39
<212> TYPE: DNA
<213> ORGANISM: Artificial Sequence
<220> FEATURE:
<223> OTHER INFORMATION: Synthetic

<400> SEQUENCE: 39
gtaaaaaggg gcgattttg gactgattat tatgactat                               39

<210> SEQ ID NO 40
<211> LENGTH: 13
<212> TYPE: PRT
<213> ORGANISM: Artificial Sequence
<220> FEATURE:
<223> OTHER INFORMATION: Synthetic

<400> SEQUENCE: 40

Val Lys Arg Gly Asp Phe Trp Thr Asp Tyr Tyr Asp Tyr
 1               5                  10

<210> SEQ ID NO 41
<211> LENGTH: 336
<212> TYPE: DNA
<213> ORGANISM: Artificial Sequence
<220> FEATURE:
<223> OTHER INFORMATION: Synthetic

<400> SEQUENCE: 41
gatattgtga tgactcagtc tccactctcc ctgcccgtca cccctggaga gccggcctcc       60
atctcctgca ggtctagtca gagcctcctt catagtaatg gacacaacta tttggattgg     120
tacctgcaga agccagggca gtctccacac ctcctgatct atttggtttc taatcgggcc     180
tccggggtcc ctgacaggtt cagtggcagt ggatcaggca cagattttac actgaaaatc     240
agcagagtgg aggctgagga tgttggagtt tattactgca tacaggctct acaaactccg     300
tggacgttcg gccaagggac caaggtggaa atcaaa                                336

<210> SEQ ID NO 42
<211> LENGTH: 112
<212> TYPE: PRT
<213> ORGANISM: Artificial Sequence
<220> FEATURE:
<223> OTHER INFORMATION: Synthetic

<400> SEQUENCE: 42

Asp Ile Val Met Thr Gln Ser Pro Leu Ser Leu Pro Val Thr Pro Gly
```

```
                 1               5                  10                 15
            Glu Pro Ala Ser Ile Ser Cys Arg Ser Ser Gln Ser Leu Leu His Ser
                             20                  25                  30

Asn Gly His Asn Tyr Leu Asp Trp Tyr Leu Gln Lys Pro Gly Gln Ser
                         35                  40                  45

Pro His Leu Leu Ile Tyr Leu Val Ser Asn Arg Ala Ser Gly Val Pro
                     50                  55                  60

Asp Arg Phe Ser Gly Ser Gly Ser Gly Thr Asp Phe Thr Leu Lys Ile
             65                  70                  75                  80

Ser Arg Val Glu Ala Glu Asp Val Gly Val Tyr Tyr Cys Ile Gln Ala
                             85                  90                  95

Leu Gln Thr Pro Trp Thr Phe Gly Gln Gly Thr Lys Val Glu Ile Lys
                        100                 105                 110
```

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43
cagagcctcc ttcatagtaa tggacacaac tat         33

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

```
Gln Ser Leu Leu His Ser Asn Gly His Asn Tyr
 1               5                  10
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 ttggtttct         9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

```
Leu Val Ser
 1
```

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atacaggctc tacaaactcc gtggacg 27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Ile Gln Ala Leu Gln Thr Pro Trp Thr
 1               5

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tgcaggagtc gggcccagga ctggtgcagc cttcacagac cctgtccctc    60
acctgcactg tctctggtgg ctccgtcagc agtggtgact actactggag ctggatccgc   120
cagcacccag ggaagggcct ggagtggatt ggacacatct attacagtgg gatcacctac   180
tacaacccgt ccctcgagag tcgagttacc ataacactgg acacgtctaa gaaccagttc   240
tccctgaacc tgagatctgt gactgccgcg gacacggccg tgcattactg tgcgagaacg   300
gctataattg gaactatgga caactggggc cggggaaccc tggtcaccgt ctcctca      357

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Glu Ser Gly Pro Gly Leu Val Gln Pro Ser Gln
 1               5                  10                  15

Thr Leu Ser Leu Thr Cys Thr Val Ser Gly Gly Ser Val Ser Ser Gly
            20                  25                  30

Asp Tyr Tyr Trp Ser Trp Ile Arg Gln His Pro Gly Lys Gly Leu Glu
        35                  40                  45

Trp Ile Gly His Ile Tyr Tyr Ser Gly Ile Thr Tyr Tyr Asn Pro Ser
 50                  55                  60

Leu Glu Ser Arg Val Thr Ile Thr Leu Asp Thr Ser Lys Asn Gln Phe
65                  70                  75                  80

Ser Leu Asn Leu Arg Ser Val Thr Ala Ala Asp Thr Ala Val His Tyr
                85                  90                  95

Cys Ala Arg Thr Ala Ile Ile Gly Thr Met Asp Asn Trp Gly Arg Gly
            100                 105                 110

Thr Leu Val Thr Val Ser Ser
        115

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
ggtggctccg tcagcagtgg tgactactac                                30

<210> SEQ ID NO 52
<211> LENGTH: 10
<212> TYPE: PRT
<213> ORGANISM: Artificial Sequence
<220> FEATURE:
<223> OTHER INFORMATION: Synthetic

<400> SEQUENCE: 52

Gly Gly Ser Val Ser Ser Gly Asp Tyr Tyr
 1               5                  10

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
atctattaca gtgggatcac c                                         21

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Tyr Tyr Ser Gly Ile Thr
 1               5

<210> SEQ ID NO 55
<211> LENGTH: 33
<212> TYPE: DNA
<213> ORGANISM: Artificial Sequence
<220> FEATURE:
<223> OTHER INFORMATION: Synthetic

<400> SEQUENCE: 55
gcgagaacgg ctataattgg aactatggac aac                            33

<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Ala Arg Thr Ala Ile Ile Gly Thr Met Asp Asn
 1               5                  10

<210> SEQ ID NO 57
<211> LENGTH: 318
<212> TYPE: DNA
<213> ORGANISM: Artificial Sequence
<220> FEATURE:
<223> OTHER INFORMATION: Synthetic

<400> SEQUENCE: 57
gaaatagtga tgacgcagtc tccagccacc ctgtctgtgt ctccagggga aagagccact    60

```
ctctcctgca gggccagtca gagtgttagc agcaacttag cctggtacca gcagaaacct    120
ggccaggctc ccaggctcct catctatgat gcatccacca gggccactgg tttcccagcc    180
aggttcagtg gcagtgggtc tgggacagaa ttcactctca ccatcagcag cctgcagtct    240
gaagattttg cagtttatta ctgtcagcaa tataatacct ggtggacgtt cggccaaggg    300
accaaggtgg aaatcaaa                                                  318
```

```
<210> SEQ ID NO 58
<211> LENGTH: 106
<212> TYPE: PRT
<213> ORGANISM: Artificial Sequence
<220> FEATURE:
<223> OTHER INFORMATION: Synthetic

<400> SEQUENCE: 58

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Trp Trp Thr
                85                  90                  95

Phe Gly Gln Gly Thr Lys Val Glu Ile Lys
            100                 105
```

```
<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagagtgtta gcagcaac                                                   18
```

```
<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ser Val Ser Ser Asn
 1               5
```

```
<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gatgcatcc                                                              9
```

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Asp Ala Ser
 1

<210> SEQ ID NO 63
<211> LENGTH: 24
<212> TYPE: DNA
<213> ORGANISM: Artificial Sequence
<220> FEATURE:
<223> OTHER INFORMATION: Synthetic

<400> SEQUENCE: 63
cagcaatata atacctggtg gacg                                                24

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Thr Trp Trp Thr
 1               5

<210> SEQ ID NO 65
<211> LENGTH: 360
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtacagc ctgggggggtc cctgagactc       60 tcctgtgcag cctctggatt caccttcagt agttacgaca tgcactgggt ccgccaaact      120
acaggaaaag gtctagagtg ggtctcaggt attggtactg ctggagatac atactatcca      180
ggctccgtga agggccgatt caccatctcc agagaagatg ccaagaattc cctgtatctt      240
caaatgaata gcctgagagc cggggacacg gctgtatatt actgtgcaag agtgggatat      300
gactggaact tcgtcgcatt tgactactgg ggccagggaa ccctggtcac cgtctcctca      360

<210> SEQ ID NO 66
<211> LENGTH: 120
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Thr Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Val Gly Tyr Asp Trp Asn Phe Val Ala Phe Asp Tyr Trp Gly Gln
            100                 105                 110

Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct tcagtagtta cgac                                          24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Ser Tyr Asp
1               5

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
attggtactg ctggagatac a                                             21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile Gly Thr Ala Gly Asp Thr
1               5

<210> SEQ ID NO 71
<211> LENGTH: 42
<212> TYPE: DNA
<213> ORGANISM: Artificial Sequence
<220> FEATURE:
<223> OTHER INFORMATION: Synthetic

<400> SEQUENCE: 71
gcaagagtgg gatatgactg gaacttcgtc gcatttgact ac                      42

<210> SEQ ID NO 72

```
<211> LENGTH: 14
<212> TYPE: PRT
<213> ORGANISM: Artificial Sequence
<220> FEATURE:
<223> OTHER INFORMATION: Synthetic

<400> SEQUENCE: 72

Ala Arg Val Gly Tyr Asp Trp Asn Phe Val Ala Phe Asp Tyr
 1               5                  10

<210> SEQ ID NO 73
<211> LENGTH: 336
<212> TYPE: DNA
<213> ORGANISM: Artificial Sequence
<220> FEATURE:
<223> OTHER INFORMATION: Synthetic

<400> SEQUENCE: 73
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtcgccacag ctcctgatcc acttggtctc tattcgggcc   180
tccggggtcc ctgacaggtt cagtggcagt ggatcaggca cagattttac acttaaaatc   240
agcagagtgg aggctgagga tgttggggatt tattactgca tgcaagctct tcaaactccg   300
tggacgttcg gccaagggac caaggtggaa atcaaa                              336

<210> SEQ ID NO 74
<211> LENGTH: 112
<212> TYPE: PRT
<213> ORGANISM: Artificial Sequence
<220> FEATURE:
<223> OTHER INFORMATION: Synthetic

<400> SEQUENCE: 74

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile His Leu Val Ser Ile Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 75
<211> LENGTH: 33
<212> TYPE: DNA
<213> ORGANISM: Artificial Sequence
<220> FEATURE:
<223> OTHER INFORMATION: Synthetic

<400> SEQUENCE: 75
cagagcctcc tgcatagtaa tggatacaac tat                                  33

<210> SEQ ID NO 76
<211> LENGTH: 11
```

<212> TYPE: PRT
<213> ORGANISM: Artificial Sequence
<220> FEATURE:
<223> OTHER INFORMATION: Synthetic

<400> SEQUENCE: 76

Gln Ser Leu Leu His Ser Asn Gly Tyr Asn Tyr
 1               5                  10

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 ttggtctct                                                            9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Leu Val Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
atgcaagctc ttcaaactcc gtggacg                                       27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Met Gln Ala Leu Gln Thr Pro Trp Thr
 1               5

<210> SEQ ID NO 81
<211> LENGTH: 357
<212> TYPE: DNA
<213> ORGANISM: Artificial Sequence
<220> FEATURE:
<223> OTHER INFORMATION: Synthetic

<400> SEQUENCE: 81
caggtgcagc tgcaggagtc gggcccagga ctggtgaagc cttcacagac cctgtccctc      60
acctgcactg tctctggtgg ctccgtcagc agtggtgatt actactggag ctggatccgc     120
cagcacccag ggaagggcct ggactggatt gggcacatct attacagtgg gagcacctac     180
tacaacccgt ccctcaagag tcgagttacc atatcactag acacgtctaa gaaccagttc     240
tccctgaagc tgaactctgt gactgccgcg gacacggccg tgtattactg tgcgagaacg     300
gctataactg gaactatgga ctactggggc agggaaccc tggtcaccgt ctcctca       357

<210> SEQ ID NO 82
<211> LENGTH: 119
<212> TYPE: PRT
<213> ORGANISM: Artificial Sequence
<220> FEATURE:
<223> OTHER INFORMATION: Synthetic

<400> SEQUENCE: 82

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Val Ser Ser Gly
            20                  25                  30

Asp Tyr Tyr Trp Ser Trp Ile Arg Gln His Pro Gly Lys Gly Leu Asp
        35                  40                  45

Trp Ile Gly His Ile Tyr Tyr Ser Gly Ser Thr Tyr Tyr Asn Pro Ser
    50                  55                  60

Leu Lys Ser Arg Val Thr Ile Ser Leu Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Thr Ala Ile Thr Gly Thr Met Asp Tyr Trp Gly Gln Gly
            100                 105                 110

Thr Leu Val Thr Val Ser Ser
        115

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
ggtggctccg tcagcagtgg tgattactac                                    30

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Gly Ser Val Ser Ser Gly Asp Tyr Tyr
 1               5                  10

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
atctattaca gtgggagcac c                                             21

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ile Tyr Tyr Ser Gly Ser Thr
 1               5

<210> SEQ ID NO 87
<211> LENGTH: 33
<212> TYPE: DNA
<213> ORGANISM: Artificial Sequence
<220> FEATURE:
<223> OTHER INFORMATION: Synthetic

<400> SEQUENCE: 87
gcgagaacgg ctataactgg aactatggac tac                                    33

<210> SEQ ID NO 88
<211> LENGTH: 11
<212> TYPE: PRT
<213> ORGANISM: Artificial Sequence
<220> FEATURE:
<223> OTHER INFORMATION: Synthetic

<400> SEQUENCE: 88

Ala Arg Thr Ala Ile Thr Gly Thr Met Asp Tyr
 1               5                  10

<210> SEQ ID NO 89
<211> LENGTH: 318
<212> TYPE: DNA
<213> ORGANISM: Artificial Sequence
<220> FEATURE:
<223> OTHER INFORMATION: Synthetic

<400> SEQUENCE: 89
gaaatagtga tgacgcagtc tccagccacc ctgtctgtgt ctgcagggga gagagccacc        60
ctctcctgca gggccagtca gagtgttagc agcaacttag cctggttcca gcagaaacct       120
ggccaggctc ccaggctcct catctatgat gcatctacca gggccactgg catcccagcc       180
aggttcagtg gcagtgggtc tgggacagag ttcactctca tcatcagcag cctgcagtct       240
gaagattttg cactttatta ctgtcagcag tataatagct ggtggacgtt cggccaaggg       300
accaaggtgg aaatcaaa                                                    318

<210> SEQ ID NO 90
<211> LENGTH: 106
<212> TYPE: PRT
<213> ORGANISM: Artificial Sequence
<220> FEATURE:
<223> OTHER INFORMATION: Synthetic

<400> SEQUENCE: 90

Glu Ile Val Met Thr Gln Ser Pro Ala Thr Leu Ser Val Ser Ala Gly
 1               5                  10                  15

Glu Arg Ala Thr Leu Ser Cys Arg Ala Ser Gln Ser Val Ser Ser Asn
                20                  25                  30

Leu Ala Trp Phe Gln Gln Lys Pro Gly Gln Ala Pro Arg Leu Leu Ile
            35                  40                  45

Tyr Asp Ala Ser Thr Arg Ala Thr Gly Ile Pro Ala Arg Phe Ser Gly
        50                  55                  60

Ser Gly Ser Gly Thr Glu Phe Thr Leu Ile Ile Ser Ser Leu Gln Ser
65                  70                  75                  80

Glu Asp Phe Ala Leu Tyr Tyr Cys Gln Gln Tyr Asn Ser Trp Trp Thr
            85                  90                  95

Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagtgtta gcagcaac                                                 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Val Ser Ser Asn
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gatgcatct                                                            9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Asp Ala Ser
 1

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
cagcagtata atagctggtg gacg                                          24

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Ser Trp Trp Thr
 1               5

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97

```
gaggtgcagc tggtggagtc tgggggaggc ttggtgcagc ctggcgggtc cctgagactc     60
tcctgtgcag cctctggatt cacctttgat gattttgcca ttcactgggt ccggcaaact    120
ccagggaggg gcctggagtg ggtctcaggt cttagttgga atagtgctta catagcctat    180
gcggactctg tgaagggccg attcaccatc tccagagaca acgccaagga ctccctctat    240
ctgcaaatga acagtctgag acctgaggac acggccttgt attactgtgt aaaagataca    300
gacatacacc tttggttttct ctttgacttc tggggccagg gaaccctggt caccgtctcc    360
tca                                                                  363
```

<210> SEQ ID NO 98
<211> LENGTH: 121
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Phe
            20                  25                  30

Ala Ile His Trp Val Arg Gln Thr Pro Gly Arg Gly Leu Glu Trp Val
        35                  40                  45

Ser Gly Leu Ser Trp Asn Ser Ala Tyr Ile Ala Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Pro Glu Asp Thr Ala Leu Tyr Tyr Cys
                85                  90                  95

Val Lys Asp Thr Asp Ile His Leu Trp Phe Leu Phe Asp Phe Trp Gly
            100                 105                 110

Gln Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct ttgatgattt tgcc                                            24
```

<210> SEQ ID NO 100
<211> LENGTH: 8
<212> TYPE: PRT
<213> ORGANISM: Artificial Sequence
<220> FEATURE:

<223> OTHER INFORMATION: Synthetic

<400> SEQUENCE: 100

Gly Phe Thr Phe Asp Asp Phe Ala
 1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
cttagttgga atagtgctta cata                                              24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Leu Ser Trp Asn Ser Ala Tyr Ile
 1               5

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gtaaaagata cagacataca cctttggttt ctctttgact tc                          42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Val Lys Asp Thr Asp Ile His Leu Trp Phe Leu Phe Asp Phe
 1               5                   10

<210> SEQ ID NO 105
<211> LENGTH: 318
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccttccacc ctgtctgcat ctgtaggaga cagagtcacc        60
atcacttgcc gggccagtca gagtattagt agttggttgg cctggtatca acagaaacca      120
gggaaagccc ctaaactcct gatctataag gcgtctagtt tagaaagtgg ggtcccatcg      180
aggttcagcg gcagtggatc tgggacagaa ttcactctca ccatcagcag cctgcagcct      240
gatgattttg caacttatta ctgccaacaa tataatagtt attcgacgtt cggccaaggg      300
acacgactgg agattaaa                                                    318

<210> SEQ ID NO 106
<211> LENGTH: 106
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagtatta gtagttgg                                                   18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Trp
1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 aaggcgtct                                                              9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Lys Ala Ser
1

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
caacaatata atagttattc gacg                                              24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Gln Gln Tyr Asn Ser Tyr Ser Thr
 1               5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggg ttggtacagc ctggggggtc cctgagactc        60
tcctgtgcag cctctggatt cacctttagc agctatgaca tgagctgggt ccgccaggct       120
ccagggaagg ggctggagtg ggtctcaggt atcagtggta gtggagatag cacatactac       180
gcaggctccg tgaagggccg gttcaccatc tccagagaca attccaagaa cactctgtat       240
ctgcaaatga acagcctgag agccgaggac acggccgtat attactgtgc gtatgactac       300
agtaactact gggaccacta cggtatggac gtctggggcc aagggaccac ggtcaccgtc       360
tcctca                                                                 366

<210> SEQ ID NO 114
<211> LENGTH: 122
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Ser Gly Ser Gly Asp Ser Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Asp Tyr Ser Asn Tyr Trp Asp His Tyr Gly Met Asp Val Trp
            100                 105                 110

Gly Gln Gly Thr Thr Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttagcagcta tgac                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Ser Tyr Asp
 1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atcagtggta gtggagatag caca                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Gly Ser Gly Asp Ser Thr
 1               5

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgtatgact acagtaacta ctgggaccac tacggtatgg acgtc                   45

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Ala Tyr Asp Tyr Ser Asn Tyr Trp Asp His Tyr Gly Met Asp Val

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatactt attctcggac gttcggccaa     300
gggaccaagg tggaaatcaa a                                                321
```

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

```
Asp Ile Gln Met Thr Gln Ser Pro Ser Thr Leu Ser Ala Ser Val Gly
  1               5                  10                  15
Asp Arg Val Thr Ile Thr Cys Arg Ala Ser Gln Ser Ile Ser Ser Trp
                 20                  25                  30
Leu Ala Trp Tyr Gln Gln Lys Pro Gly Lys Ala Pro Lys Leu Leu Ile
             35                  40                  45
Tyr Lys Ala Ser Ser Leu Glu Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Tyr Asn Thr Tyr Ser Arg
                 85                  90                  95
Thr Phe Gly Gln Gly Thr Lys Val Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
cagagtatta gtagctgg                                                     18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

```
Gln Ser Ile Ser Ser Trp
  1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 aaggcgtct                                                                  9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Lys Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagtata atacttattc tcggacg                                             27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Asn Thr Tyr Ser Arg Thr
 1               5

<210> SEQ ID NO 129
<211> LENGTH: 360
<212> TYPE: DNA
<213> ORGANISM: Artificial Sequence
<220> FEATURE:
<223> OTHER INFORMATION: Synthetic

<400> SEQUENCE: 129
caggtgcagc tgcaggagtc gggcccagga ctggtgaagc cttcacagac cctgtccctc         60
acctgcactg tctctggtgg ctccatcagc agtggtgatt actactggaa ctggatccgc        120
cagtacccag ggaagggcct ggagttgatt ggctacatct attacagtgg aatcacctac        180
tacaacccgt ccctcaagag tcgacttacc atttcattag acacgtctaa gaaccagttc        240
tccctgaagc tgagttctgt gactgccgcg gacacggccg tgtattactg tgcgagagat        300
agagtggaac tacgggcttt tgatatctgg ggccaaggga caatggtcac cgtctcttca        360

<210> SEQ ID NO 130
<211> LENGTH: 120
<212> TYPE: PRT
<213> ORGANISM: Artificial Sequence
<220> FEATURE:

<223> OTHER INFORMATION: Synthetic

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Asn Trp Ile Arg Gln Tyr Pro Gly Lys Gly Leu Glu
        35                  40                  45

Leu Ile Gly Tyr Ile Tyr Tyr Ser Gly Ile Thr Tyr Tyr Asn Pro Ser
    50                  55                  60

Leu Lys Ser Arg Leu Thr Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Val Glu Leu Arg Ala Phe Asp Ile Trp Gly Gln
            100                 105                 110

Gly Thr Met Val Thr Val Ser Ser
        115                 120

<210> SEQ ID NO 131
<211> LENGTH: 30
<212> TYPE: DNA
<213> ORGANISM: Artificial Sequence
<220> FEATURE:
<223> OTHER INFORMATION: Synthetic

<400> SEQUENCE: 131
ggtggctcca tcagcagtgg tgattactac                                    30

<210> SEQ ID NO 132
<211> LENGTH: 10
<212> TYPE: PRT
<213> ORGANISM: Artificial Sequence
<220> FEATURE:
<223> OTHER INFORMATION: Synthetic

<400> SEQUENCE: 132

Gly Gly Ser Ile Ser Ser Gly Asp Tyr Tyr
1               5                   10

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
atctattaca gtggaatcac c                                             21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Tyr Tyr Ser Gly Ile Thr
1               5

```
<210> SEQ ID NO 135
<211> LENGTH: 36
<212> TYPE: DNA
<213> ORGANISM: Artificial Sequence
<220> FEATURE:
<223> OTHER INFORMATION: Synthetic

<400> SEQUENCE: 135
gcgagagata gagtggaact acgggctttt gatatc                                    36

<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

Ala Arg Asp Arg Val Glu Leu Arg Ala Phe Asp Ile
 1               5                  10

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctgtaggaga cagagtcacc          60
atcacttgcc aggcgagtca ggacattagt aactatttaa attggtatca gcagaaacca        120
gggaaagccc ctaaactcct gatcaacgat gcatccaatt tggaaacagg ggtcccatca        180
aggttcagtg gaagtggatc tgggacagat tttacttttca ccatcagcag cctgcagcct        240
gaagatattg caacatatta ctgtcaacat tatgatagtc tccctctcac cttcggccaa        300
gggacacgac tggagattaa a                                                  321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Asn Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Tyr Asp Ser Leu Pro Leu
                85                  90                  95

Thr Phe Gly Gln Gly Thr Arg Leu Glu Ile Lys
            100                 105

<210> SEQ ID NO 139
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggacatta gtaactat                                                 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asp Ile Ser Asn Tyr
 1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gatgcatcc                                                            9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Asp Ala Ser
 1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacattatg atagtctccc tctcacc                                       27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln His Tyr Asp Ser Leu Pro Leu Thr
 1               5

<210> SEQ ID NO 145
<211> LENGTH: 360
<212> TYPE: DNA
<213> ORGANISM: Artificial Sequence
<220> FEATURE:
```

<223> OTHER INFORMATION: Synthetic

<400> SEQUENCE: 145

```
caggtgcagc tgcaggagtc gggcccagga ctggtgaagc cttcacagac cctgtccctc    60
acctgcactg tctctggtgg ctccatcagc agtggtgatt actactggaa ctggatccgc   120
cagtacccag ggaagggcct ggagttgatt ggctacatct attacagtgg aatcacctac   180
tacaacccgt ccctcaagag tcgacttacc atttcattag acacgtctaa gaaccagttc   240
tccctgaagc tgagttctgt gactgccgcg gacacggccg tgtattactg tgcgagagat   300
agagtggaac tacgagcttt tgatatctgg ggccaaggga caatggtcac cgtctcttca   360
```

<210> SEQ ID NO 146
<211> LENGTH: 120
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Asp Tyr Tyr Trp Asn Trp Ile Arg Gln Tyr Pro Gly Lys Gly Leu Glu
         35                  40                  45

Leu Ile Gly Tyr Ile Tyr Tyr Ser Gly Ile Thr Tyr Tyr Asn Pro Ser
     50                  55                  60

Leu Lys Ser Arg Leu Thr Ile Ser Leu Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Arg Val Glu Leu Arg Ala Phe Asp Ile Trp Gly Gln
            100                 105                 110

Gly Thr Met Val Thr Val Ser Ser
        115                 120
```

<210> SEQ ID NO 147
<211> LENGTH: 30
<212> TYPE: DNA
<213> ORGANISM: Artificial Sequence
<220> FEATURE:
<223> OTHER INFORMATION: Synthetic

<400> SEQUENCE: 147

```
ggtggctcca tcagcagtgg tgattactac                                     30
```

<210> SEQ ID NO 148
<211> LENGTH: 10
<212> TYPE: PRT
<213> ORGANISM: Artificial Sequence
<220> FEATURE:
<223> OTHER INFORMATION: Synthetic

<400> SEQUENCE: 148

```
Gly Gly Ser Ile Ser Ser Gly Asp Tyr Tyr
  1               5                  10
```

<210> SEQ ID NO 149
<211> LENGTH: 21
<212> TYPE: DNA

<213> ORGANISM: Artificial Sequence
<220> FEATURE:
<223> OTHER INFORMATION: Synthetic

<400> SEQUENCE: 149
atctattaca gtggaatcac c                                              21

<210> SEQ ID NO 150
<211> LENGTH: 7
<212> TYPE: PRT
<213> ORGANISM: Artificial Sequence
<220> FEATURE:
<223> OTHER INFORMATION: Synthetic

<400> SEQUENCE: 150

Ile Tyr Tyr Ser Gly Ile Thr
1               5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
gcgagagata gagtggaact acgagctttt gatatc                              36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ala Arg Asp Arg Val Glu Leu Arg Ala Phe Asp Ile
1               5                   10

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctataggaga cagaatcacc    60
atctcttgcc aggcgagtca ggacattaac aactatttaa attggtatca gcagaaacca   120
gggaaagccc ctaaactcct gatctacgat gcatccaatt tggaaacagg gatcccatca   180
aggttcagtg gaagtggatc tgggacagat tttactttca ccatcagcgg cctgcagcct   240
gaagatattg caacatatta ctgtcaaaca tatgatagtc tccctctcac cttcggccaa   300
gggacacgac tggagattaa a                                             321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Ile Gly

```
                1               5                   10                  15
            Asp Arg Ile Thr Ile Ser Cys Gln Ala Ser Gln Asp Ile Asn Asn Tyr
                                20                  25                  30

Leu Asn Trp Tyr Gln Gln Lys Pro Gly Lys Ala Pro Lys Leu Leu Ile
                        35                  40                  45

Tyr Asp Ala Ser Asn Leu Glu Thr Gly Ile Pro Ser Arg Phe Ser Gly
                    50                  55                  60

Ser Gly Ser Gly Thr Asp Phe Thr Phe Thr Ile Ser Gly Leu Gln Pro
             65                  70                  75                  80

Glu Asp Ile Ala Thr Tyr Tyr Cys Gln His Tyr Asp Ser Leu Pro Leu
                            85                  90                  95

Thr Phe Gly Gln Gly Thr Arg Leu Glu Ile Lys
                            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
caggacatta acaactat                                                     18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Asn Asn Tyr
 1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gatgcatcc                                                                9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Asp Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
```
caacactatg atagtctccc tctcacc    27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln His Tyr Asp Ser Leu Pro Leu Thr
1               5

<210> SEQ ID NO 161
<211> LENGTH: 360
<212> TYPE: DNA
<213> ORGANISM: Artificial Sequence
<220> FEATURE:
<223> OTHER INFORMATION: Synthetic

<400> SEQUENCE: 161
caggtgcagc tgcaggagtc gggcccagga ctggtgatgc cttcacagac cctgtccctc    60
acctgcactg tctctggtgg ctccatcaac agtggtgatt actactggaa ctggatccgc   120
cagcacccag ggaagggcct ggagtggatt ggatacatct attacagtga aatcagttat   180
cacaacccgt ccctcaagag tcgagttacc acctcaatag acacgtctac gaaccagttc   240
tccctgaagc tgagctctgt gactgccgcg gacacggccg tctattactg tgcgagagat   300
agagtggaac tacgagcttt tgatatctgg ggccaaggga caatggtcac cgtctcttca   360

<210> SEQ ID NO 162
<211> LENGTH: 120
<212> TYPE: PRT
<213> ORGANISM: Artificial Sequence
<220> FEATURE:
<223> OTHER INFORMATION: Synthetic

<400> SEQUENCE: 162

Gln Val Gln Leu Gln Glu Ser Gly Pro Gly Leu Val Met Pro Ser Gln
1               5                   10                  15

Thr Leu Ser Leu Thr Cys Thr Val Ser Gly Gly Ser Ile Asn Ser Gly
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Glu Ile Ser Tyr His Asn Pro Ser
    50                  55                  60

Leu Lys Ser Arg Val Thr Thr Ser Ile Asp Thr Ser Thr Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Val Glu Leu Arg Ala Phe Asp Ile Trp Gly Gln
            100                 105                 110

Gly Thr Met Val Thr Val Ser Ser
        115                 120

<210> SEQ ID NO 163
<211> LENGTH: 30
<212> TYPE: DNA
<213> ORGANISM: Artificial Sequence
<220> FEATURE:
<223> OTHER INFORMATION: Synthetic

```
<400> SEQUENCE: 163
ggtggctcca tcaacagtgg tgattactac                                         30

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Gly Gly Ser Ile Asn Ser Gly Asp Tyr Tyr
 1               5                  10

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
atctattaca gtgaaatcag t                                                  21

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Tyr Tyr Ser Glu Ile Ser
 1               5

<210> SEQ ID NO 167
<211> LENGTH: 36
<212> TYPE: DNA
<213> ORGANISM: Artificial Sequence
<220> FEATURE:
<223> OTHER INFORMATION: Synthetic

<400> SEQUENCE: 167
gcgagagata gagtggaact acgagctttt gatatc                                  36

<210> SEQ ID NO 168
<211> LENGTH: 12
<212> TYPE: PRT
<213> ORGANISM: Artificial Sequence
<220> FEATURE:
<223> OTHER INFORMATION: Synthetic

<400> SEQUENCE: 168

Ala Arg Asp Arg Val Glu Leu Arg Ala Phe Asp Ile
 1               5                  10

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtaggaga cagagtcacc        60
```

```
atcacttgcc aggcgagtca ggacattagc aactatttaa attggtatca gcagaaacca    120
gggaaagccc ctaaactcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacac tatgatagtc tccctctcac cttcggccaa    300
gggacacgac tggagattaa a                                              321
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Tyr Asp Ser Leu Pro Leu
                85                  90                  95

Thr Phe Gly Gln Gly Thr Arg Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
caggacatta gcaactat                                                   18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Asp Ile Ser Asn Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gatgcatcc                                                              9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Asp Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacactatg atagtctccc tctcacc                                           27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln His Tyr Asp Ser Leu Pro Leu Thr
 1               5

<210> SEQ ID NO 177
<211> LENGTH: 360
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtgatgc cttcacagac cctgtccctc      60
acctgcactg tctctggtgg ctccatcaac agtggtgatt actactggaa ctggatccgc     120
cagcacccag ggaagggcct ggagtggatt ggatacatct attacagtga atcagttat      180 cacaacccgt ccctcaagag tcgagttacc acctcaatag acacgtctac gaaccagttc    240
tccctgaagc tgagctctgt gactgccgcg gacacggccg tctattactg tgcgagagat    300
agagtggaac tacgagcttt tgatatctgg ggccaaggga caatggtcac cgtctcttca    360

<210> SEQ ID NO 178
<211> LENGTH: 120
<212> TYPE: PRT
<213> ORGANISM: Artificial Sequence
<220> FEATURE:
<223> OTHER INFORMATION: Synthetic

<400> SEQUENCE: 178

Gln Val Gln Leu Gln Glu Ser Gly Pro Gly Leu Val Met Pro Ser Gln
 1               5                  10                  15

Thr Leu Ser Leu Thr Cys Thr Val Ser Gly Gly Ser Ile Asn Ser Gly
                20                  25                  30

Asp Tyr Tyr Trp Asn Trp Ile Arg Gln His Pro Gly Lys Gly Leu Glu
            35                  40                  45

```
Trp Ile Gly Tyr Ile Tyr Tyr Ser Glu Ile Ser Tyr His Asn Pro Ser
     50                  55                  60

Leu Lys Ser Arg Val Thr Thr Ser Ile Asp Thr Ser Thr Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Asp Arg Val Glu Leu Arg Ala Phe Asp Ile Trp Gly Gln
            100                 105                 110

Gly Thr Met Val Thr Val Ser Ser
            115                 120
```

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179
ggtggctcca tcaacagtgg tgattactac         30

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

```
Gly Gly Ser Ile Asn Ser Gly Asp Tyr Tyr
 1               5                  10
```

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
atctattaca gtgaaatcag t         21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

```
Ile Tyr Tyr Ser Glu Ile Ser
 1               5
```

<210> SEQ ID NO 183
<211> LENGTH: 36
<212> TYPE: DNA
<213> ORGANISM: Artificial Sequence
<220> FEATURE:
<223> OTHER INFORMATION: Synthetic

<400> SEQUENCE: 183
gcgagagata gagtggaact acgagctttt gatatc         36

<210> SEQ ID NO 184

```
<211> LENGTH: 12
<212> TYPE: PRT
<213> ORGANISM: Artificial Sequence
<220> FEATURE:
<223> OTHER INFORMATION: Synthetic

<400> SEQUENCE: 184

Ala Arg Asp Arg Val Glu Leu Arg Ala Phe Asp Ile
 1               5                  10

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcctcc ctgtctgcat ctgttggaga cagagtcacc    60
atcacttgcc aggcgagtca ggacattagc aactatttaa attggtatca gcagaaacca   120
gggaaagccc ctaaactcct gatctacgat gcatccaatt tggagacagg ggtcccatca   180
aggttcagtg gaagtggatc tgggacagat tttactttca ccatcagcag cctgcagcct   240
gaagatattg caacatatta ctgtcaacac tatgatagtc tccctctcac cttcggccaa   300
gggacacgac tggagattaa a                                              321

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Tyr Asp Ser Leu Pro Leu
                85                  90                  95

Thr Phe Gly Gln Gly Thr Arg Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
caggacatta gcaactat                                                   18

<210> SEQ ID NO 188
<211> LENGTH: 6
```

```
<212> TYPE: PRT
<213> ORGANISM: Artificial Sequence
<220> FEATURE:
<223> OTHER INFORMATION: Synthetic

<400> SEQUENCE: 188

Gln Asp Ile Ser Asn Tyr
 1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gatgcatcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Asp Ala Ser
 1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacactatg atagtctccc tctcacc                                             27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln His Tyr Asp Ser Leu Pro Leu Thr
 1               5

<210> SEQ ID NO 193
<211> LENGTH: 384
<212> TYPE: DNA
<213> ORGANISM: Artificial Sequence
<220> FEATURE:
<223> OTHER INFORMATION: Synthetic

<400> SEQUENCE: 193
gaggtgcagc tggtggagtc tgggggaggc gtggtacagc ctggggggtc cctgagactc         60
tcctgtgcag cctctggatt cacctttgat gattatgcca tgcactgggt ccgtcaagct        120
ccagggaagg gtctggagtg ggtctctctt attagtgggg atggtggtag cacatactat        180
gcagactctg tgaagggccg attcaccatc tccagagaca acagcaaaaa ctccctgtat        240
ctgcaaatga acagtctgag aactgaggac accgccttgt attactgtgc aaaaaattat        300
```

```
gatagtagtg gttattacta cccttactac tactactacg gtatggacgt ctggggccaa    360
gggaccacgg tcaccgtctc ctca                                          384
```

<210> SEQ ID NO 194
<211> LENGTH: 128
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Leu Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asn Tyr Asp Ser Ser Gly Tyr Tyr Tyr Pro Tyr Tyr Tyr Tyr
            100                 105                 110

Tyr Gly Met Asp Val Trp Gly Gln Gly Thr Thr Val Thr Val Ser Ser
        115                 120                 125
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggattcacct ttgatgatta tgcc                                          24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Phe Asp Asp Tyr Ala
 1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

```
attagtgggg atggtggtag caca                                          24
```

<210> SEQ ID NO 198
<211> LENGTH: 8

<212> TYPE: PRT
<213> ORGANISM: Artificial Sequence
<220> FEATURE:
<223> OTHER INFORMATION: Synthetic

<400> SEQUENCE: 198

Ile Ser Gly Asp Gly Gly Ser Thr
 1               5

<210> SEQ ID NO 199
<211> LENGTH: 63
<212> TYPE: DNA
<213> ORGANISM: Artificial Sequence
<220> FEATURE:
<223> OTHER INFORMATION: Synthetic

<400> SEQUENCE: 199
gcaaaaaatt atgatagtag tggttattac taccttact actactacta cggtatggac    60
gtc                                                                 63

<210> SEQ ID NO 200
<211> LENGTH: 21
<212> TYPE: PRT
<213> ORGANISM: Artificial Sequence
<220> FEATURE:
<223> OTHER INFORMATION: Synthetic

<400> SEQUENCE: 200

Ala Lys Asn Tyr Asp Ser Ser Gly Tyr Tyr Tyr Pro Tyr Tyr Tyr Tyr
 1               5                  10                  15

Tyr Gly Met Asp Val
            20

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagct tagaaagtgg ggtcccatca   180
aggttcagcg gcagtggatc tgggacagaa ttcactctca ccatcagtag cctgcagcct   240
gatgattttg caacttatta ctgccaacag tataatagtt attctcggac gttcggccaa   300
gggaccaagg tggaaatcaa a                                             321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile

```
                    35                  40                  45
Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatta gtagctgg                                                       18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggcgtct                                                                  9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagtata atagttattc tcggacg                                             27

<210> SEQ ID NO 208
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Ser Tyr Ser Arg Thr
  1               5

<210> SEQ ID NO 209
<211> LENGTH: 357
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc gggcccagga ctggtgcagc cttcacagac cctgtccctc      60
acctgcactg tctctggtgg ctccatcaac agtggtgatt tctactggag ttggatccgc     120
cagcatccag ggaagggcct ggagtggatt ggtcacatat attacagtgg gatcacctac     180
tacagtccgt ccctcaagag tcgacttacc atctcagtag acacgtctaa gaaccagttc     240
tccctgaagc tgagttctgt gactgccgcg gacacggccg tgtattactg tgcgagaaag     300
agggtaactg gggaagttga ctactggggc cagggaaccc tggtcaccgt ctcctca       357

<210> SEQ ID NO 210
<211> LENGTH: 119
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Pro Gly Leu Val Gln Pro Ser Gln
  1               5                  10                  15

Thr Leu Ser Leu Thr Cys Thr Val Ser Gly Gly Ser Ile Asn Ser Gly
             20                  25                  30

Asp Phe Tyr Trp Ser Trp Ile Arg Gln His Pro Gly Lys Gly Leu Glu
         35                  40                  45

Trp Ile Gly His Ile Tyr Tyr Ser Gly Ile Thr Tyr Tyr Ser Pro Ser
     50                  55                  60

Leu Lys Ser Arg Leu Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Lys Arg Val Thr Gly Glu Val Asp Tyr Trp Gly Gln Gly
            100                 105                 110

Thr Leu Val Thr Val Ser Ser
        115

<210> SEQ ID NO 211
<211> LENGTH: 30
<212> TYPE: DNA
<213> ORGANISM: Artificial Sequence
<220> FEATURE:
<223> OTHER INFORMATION: Synthetic

<400> SEQUENCE: 211
ggtggctcca tcaacagtgg tgatttctac                                       30
```

```
<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Gly Gly Ser Ile Asn Ser Gly Asp Phe Tyr
 1               5                  10

<210> SEQ ID NO 213
<211> LENGTH: 21
<212> TYPE: DNA
<213> ORGANISM: Artificial Sequence
<220> FEATURE:
<223> OTHER INFORMATION: Synthetic

<400> SEQUENCE: 213
atatattaca gtgggatcac c                                              21

<210> SEQ ID NO 214
<211> LENGTH: 7
<212> TYPE: PRT
<213> ORGANISM: Artificial Sequence
<220> FEATURE:
<223> OTHER INFORMATION: Synthetic

<400> SEQUENCE: 214

Ile Tyr Tyr Ser Gly Ile Thr
 1               5

<210> SEQ ID NO 215
<211> LENGTH: 33
<212> TYPE: DNA
<213> ORGANISM: Artificial Sequence
<220> FEATURE:
<223> OTHER INFORMATION: Synthetic

<400> SEQUENCE: 215
gcgagaaaga gggtaactgg ggaagttgac tac                                 33

<210> SEQ ID NO 216
<211> LENGTH: 11
<212> TYPE: PRT
<213> ORGANISM: Artificial Sequence
<220> FEATURE:
<223> OTHER INFORMATION: Synthetic

<400> SEQUENCE: 216

Ala Arg Lys Arg Val Thr Gly Glu Val Asp Tyr
 1               5                  10

<210> SEQ ID NO 217
<211> LENGTH: 324
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcctcc ctgtctgcat ctgtaggaga cagaatcacc     60
atcacttgcc aggcgaatca ggacattaac aactatttaa attggtatca gcaaagcca    120 gggaaagccc ctaagctcct gatctccgat gcatccaatt tggaaacagg ggtcccatca   180
agattcagtg gaagtggatc tgggacagat tttactttca ccatcagcag cctgcagcct   240
```

```
gaagatattg caacatatta ctgtcaacag tatgataatc tccctcccac cttcggccaa    300
gggacacgac tggagattaa acga                                          324
```

<210> SEQ ID NO 218
<211> LENGTH: 108
<212> TYPE: PRT
<213> ORGANISM: Artificial Sequence
<220> FEATURE:
<223> OTHER INFORMATION: Synthetic

<400> SEQUENCE: 218

```
Asp Ile Gln Met Thr Gln Ser Pro Ser Ser Leu Ser Ala Ser Val Gly
 1               5                  10                  15

Asp Arg Ile Thr Ile Thr Cys Gln Ala Asn Gln Asp Ile Asn Asn Tyr
             20                  25                  30

Leu Asn Trp Tyr Gln Gln Lys Pro Gly Lys Ala Pro Lys Leu Leu Ile
         35                  40                  45

Ser Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Pro
                 85                  90                  95

Thr Phe Gly Gln Gly Thr Arg Leu Glu Ile Lys Arg
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
caggacatta acaactat                                                  18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Asp Ile Asn Asn Tyr
 1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221

```
gatgcatcc                                                             9
```

<210> SEQ ID NO 222
<211> LENGTH: 3
<212> TYPE: PRT
<213> ORGANISM: Artificial Sequence
<220> FEATURE:

<223> OTHER INFORMATION: Synthetic

<400> SEQUENCE: 222

Asp Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacagtatg ataatctccc tcccacc                                       27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Asp Asn Leu Pro Pro Thr
 1               5

<210> SEQ ID NO 225
<211> LENGTH: 360
<212> TYPE: DNA
<213> ORGANISM: Artificial Sequence
<220> FEATURE:
<223> OTHER INFORMATION: Synthetic

<400> SEQUENCE: 225
caggtgcagc tgcaggagtc gggcccagga ctggtgaacc cttcacagac cctgtccctc     60
acctgcactg tctctggtgg ctccatcaat agtggtgatt actactggag ctgggtccgc    120
cagcacccag ggaagggcct ggagtggatt ggatacatct attacagtgg gagcacctac    180
tacaacccgt ccctcaagag tcgagttacc atctcagtgg acacgtctaa gaaccagttc    240
tccctgaaac tgagctctgt gactgtcgcg gacacggccg tatattactg tgcgagagtg    300
ggctacagta aagggtactt tgactcctgg ggccagggaa ccctggtcac tgtctcctca    360

<210> SEQ ID NO 226
<211> LENGTH: 120
<212> TYPE: PRT
<213> ORGANISM: Artificial Sequence
<220> FEATURE:
<223> OTHER INFORMATION: Synthetic

<400> SEQUENCE: 226

Gln Val Gln Leu Gln Glu Ser Gly Pro Gly Leu Val Asn Pro Ser Gln
 1               5                  10                  15

Thr Leu Ser Leu Thr Cys Thr Val Ser Gly Gly Ser Ile Asn Ser Gly
                20                  25                  30

Asp Tyr Tyr Trp Ser Trp Val Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Val Ala Asp Thr Ala Val Tyr Tyr
            85                  90                  95

Cys Ala Arg Val Gly Tyr Ser Lys Gly Tyr Phe Asp Ser Trp Gly Gln
        100                 105                 110

Gly Thr Leu Val Thr Val Ser Ser
        115                 120

<210> SEQ ID NO 227
<211> LENGTH: 30
<212> TYPE: DNA
<213> ORGANISM: Artificial Sequence
<220> FEATURE:
<223> OTHER INFORMATION: Synthetic

<400> SEQUENCE: 227
ggtggctcca tcaatagtgg tgattactac                                      30

<210> SEQ ID NO 228
<211> LENGTH: 10
<212> TYPE: PRT
<213> ORGANISM: Artificial Sequence
<220> FEATURE:
<223> OTHER INFORMATION: Synthetic

<400> SEQUENCE: 228

Gly Gly Ser Ile Asn Ser Gly Asp Tyr Tyr
1               5                   10

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229
atctattaca gtgggagcac c                                               21

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

Ile Tyr Tyr Ser Gly Ser Thr
1               5

<210> SEQ ID NO 231
<211> LENGTH: 36
<212> TYPE: DNA
<213> ORGANISM: Artificial Sequence
<220> FEATURE:
<223> OTHER INFORMATION: Synthetic

<400> SEQUENCE: 231
gcgagagtgg gctacagtaa agggtacttt gactcc                               36

<210> SEQ ID NO 232
<211> LENGTH: 12
<212> TYPE: PRT
<213> ORGANISM: Artificial Sequence
<220> FEATURE:
<223> OTHER INFORMATION: Synthetic

<400> SEQUENCE: 232

Ala Arg Val Gly Tyr Ser Lys Gly Tyr Phe Asp Ser
1               5                   10

<210> SEQ ID NO 233
<211> LENGTH: 318
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccttccacc ctgtctgcat ctgtaggaga cagagtcacc    60
atcacttgcc gggccagtga gagtattagt agctggttgg cctggtatca gcagaaacca   120
gggaaagccc ctaaggtcct gatctatgat gcgtctagtt tagaaagtgg ggtcccatca   180
aggttcagcg gcagtggatc tgggacagaa tacactctca ccatcagcag cctgcagcct   240
gatgactttg caagttatta ctgccaacag tataaaagtt attggacgtt cggccaaggg   300
accaaggtgg aaatcaaa                                                 318
```

<210> SEQ ID NO 234
<211> LENGTH: 106
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Ser Ser Trp
            20                  25                  30

Leu Ala Trp Tyr Gln Gln Lys Pro Gly Lys Ala Pro Lys Val Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Ser Tyr Tyr Cys Gln Gln Tyr Lys Ser Tyr Trp Thr
                85                  90                  95

Phe Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
gagagtatta gtagctgg                                                  18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

```
Glu Ser Ile Ser Ser Trp
  1               5
```

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237

```
gatgcgtct                                                                  9
```

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

```
Asp Ala Ser
  1
```

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239

```
caacagtata aaagttattg gacg                                                24
```

<210> SEQ ID NO 240
<211> LENGTH: 8
<212> TYPE: PRT
<213> ORGANISM: Artificial Sequence
<220> FEATURE:
<223> OTHER INFORMATION: Synthetic

<400> SEQUENCE: 240

```
Gln Gln Tyr Lys Ser Tyr Trp Thr
  1               5
```

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241

```
caggtgcagc tggtggagtc tgggggaggc gtggtccagc ctgggaagtc cctgagactc         60
tcctgtgcag cctctggatt caccttcagt atctatggca tgaactgggt ccgccaggct        120
ccaggcaagg ggctggactg ggtggcagtt atttcagatg atggaagtaa taagactat         180 gtggactccg tgaggggtcg attcaccatc tccagagaca attccaagaa cacgctgtat        240
ctgcaaatga acagcctgag cgctgaagac acggctgtct attactgtgc gaaagatcgt        300
atcactggca ctcattacta cggttttgga cgtctggggcc aagggaccac ggtcaccgtc      360
tcctca                                                                  366
```

```
<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Val Val Gln Pro Gly Lys
  1               5                  10                  15

Ser Leu Arg Leu Ser Cys Ala Ala Ser Gly Phe Thr Phe Ser Ile Tyr
             20                  25                  30

Gly Met Asn Trp Val Arg Gln Ala Pro Gly Lys Gly Leu Asp Trp Val
         35                  40                  45

Ala Val Ile Ser Asp Asp Gly Ser Asn Lys Asp Tyr Val Asp Ser Val
     50                  55                  60

Arg Gly Arg Phe Thr Ile Ser Arg Asp Asn Ser Lys Asn Thr Leu Tyr
 65                  70                  75                  80

Leu Gln Met Asn Ser Leu Ser Ala Glu Asp Thr Ala Val Tyr Tyr Cys
                 85                  90                  95

Ala Lys Asp Arg Ile Thr Gly Thr His Tyr Tyr Gly Leu Asp Val Trp
            100                 105                 110

Gly Gln Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtatcta tggc                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ile Tyr Gly
  1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atttcagatg atggaagtaa taaa                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246
```

Ile Ser Asp Asp Gly Ser Asn Lys
1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgaaagatc gtatcactgg cactcattac tacggtttgg acgtc          45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Lys Asp Arg Ile Thr Gly Thr His Tyr Tyr Gly Leu Asp Val
1               5                   10                  15

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccgtcctca ctgtctgcat ctgtcggaga cagaatcacc     60
atcacttgtc gggcgagtca ggacattgcc aattatttag cctggtttca gcagaaacca    120
ggtaatgccc ctacgtccct gatctatgct gcatccattt tgcaaagtgg ggtcccatca    180
aagttcagcg gcagtggatc tgggacagat ttcactctca ccatcaccag cctgcagcca    240
gaagattttg caagttatta ctgccaacaa tataatagaa agccgtggac gttcggccga    300
gggaccaagg tggaaatcaa a                                              321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Asp Ile Ala Asn Tyr
            20                  25                  30

Leu Ala Trp Phe Gln Gln Lys Pro Gly Asn Ala Pro Thr Ser Leu Ile
        35                  40                  45

Tyr Ala Ala Ser Ile Leu Gln Ser Gly Val Pro Ser Lys Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Ser Tyr Tyr Cys Gln Gln Tyr Asn Arg Lys Pro Trp
                85                  90                  95

Thr Phe Gly Arg Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
caggacattg ccaattat                                                    18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Asp Ile Ala Asn Tyr
 1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gctgcatcc                                                               9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ala Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacaatata atagaaagcc gtggacg                                          27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Arg Lys Pro Trp Thr
 1               5

<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257

```
caggtgcagc tggtggagtc tgggggaggc gtggtccagc ctggggaggtc cctgagactc      60
tcctgtgcag cctctggatt caccttcagt atctatggca tgcactgggt ccgccaggct     120
ccaggcaagg gactggagtg ggtgacagtt atatcagacg atggaagtaa aaaatactat     180
gtagactccg tgaagggccg attcaccctc tccagagaca attccaagaa cacgctgtat     240
ctgcaaatga acagcctgag agctgaggac acggctgtgt attactgtgc gagagatcgt     300
ataactggaa ccaactggta cggtatggac gtctggggcc aggggaccac ggtcaccgtc     360
tcctca                                                                366
```

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ile Tyr
            20                  25                  30
Gly Met His Trp Val Arg Gln Ala Pro Gly Lys Gly Leu Glu Trp Val
        35                  40                  45
Thr Val Ile Ser Asp Asp Gly Ser Lys Lys Tyr Tyr Val Asp Ser Val
    50                  55                  60
Lys Gly Arg Phe Thr Leu Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Ile Thr Gly Thr Asn Trp Tyr Gly Met Asp Val Trp
            100                 105                 110
Gly Gln Gly Thr Thr Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct tcagtatcta tggc                                              24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

-continued

Gly Phe Thr Phe Ser Ile Tyr Gly
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atatcagacg atggaagtaa aaaa                                            24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Asp Asp Gly Ser Lys Lys
1               5

<210> SEQ ID NO 263
<211> LENGTH: 45
<212> TYPE: DNA
<213> ORGANISM: Artificial Sequence
<220> FEATURE:
<223> OTHER INFORMATION: Synthetic

<400> SEQUENCE: 263
gcgagagatc gtataactgg aaccaactgg tacggtatgg acgtc                     45

<210> SEQ ID NO 264
<211> LENGTH: 15
<212> TYPE: PRT
<213> ORGANISM: Artificial Sequence
<220> FEATURE:
<223> OTHER INFORMATION: Synthetic

<400> SEQUENCE: 264

Ala Arg Asp Arg Ile Thr Gly Thr Asn Trp Tyr Gly Met Asp Val
1               5                   10                  15

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccatcctca ctgtctgcat ctgtaggaga cagagtcacc     60
atcacttgtc gggcgagtca ggacattagc aattatttag cctggtttca gcagaaacca    120
gggaaagccc ctaagtccct gatctttgct gcatccagtt tgcaaagtgg ggcccatca     180 aagttcagcg gcagtggatc tgggacagat ttcactctca ccatcagcag cctgcagcct    240
gaagattttg caacttatta ctgccaacag tataatcgtt acccattcac tttcggccct    300
gggaccaaag tggatatcaa a                                              321

<210> SEQ ID NO 266
<211> LENGTH: 107
<212> TYPE: PRT

<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Phe Ala Ala Ser Ser Leu Gln Ser Gly Gly Pro Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg Tyr Pro Phe
                85                  90                  95

Thr Phe Gly Pro Gly Thr Lys Val Asp Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
caggacatta gcaattat                                                 18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Asp Ile Ser Asn Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gctgcatcc                                                            9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
1

<210> SEQ ID NO 271

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
caacagtata atcgttaccc attcact             27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Tyr Asn Arg Tyr Pro Phe Thr
 1               5

<210> SEQ ID NO 273
<211> LENGTH: 366
<212> TYPE: DNA
<213> ORGANISM: Artificial Sequence
<220> FEATURE:
<223> OTHER INFORMATION: Synthetic

<400> SEQUENCE: 273
caggtgcagc tggtggagtc tgggggaggc gtggtccagc ctggggaggtc cctcagactc      60 acctgtaaag cctctggatt caccttcagt atctatggca taaactgggt ccgccaggct     120
tcaggcaagg ggctggactg ggtggcagtc atttcagatg atggaagtga taagaagtat     180
gcagattccg tgaagggccg attcaccatc tcccgagaca attccaaaaa cacggtttat     240
ctggaaatga gcagactgag aagtgaggac acggctgttt atttctgtgc gaaagaccgg     300
tttactggaa accactatta cggtatggac gtctggggcc aagggaccac ggtcaccgtc     360
tcctca                                                                366

<210> SEQ ID NO 274
<211> LENGTH: 122
<212> TYPE: PRT
<213> ORGANISM: Artificial Sequence
<220> FEATURE:
<223> OTHER INFORMATION: Synthetic

<400> SEQUENCE: 274

Gln Val Gln Leu Val Glu Ser Gly Gly Gly Val Val Gln Pro Gly Arg
 1               5                  10                  15

Ser Leu Arg Leu Thr Cys Lys Ala Ser Gly Phe Thr Phe Ser Ile Tyr
            20                  25                  30

Gly Ile Asn Trp Val Arg Gln Ala Ser Gly Lys Gly Leu Asp Trp Val
        35                  40                  45

Ala Val Ile Ser Asp Asp Gly Ser Asp Lys Lys Tyr Ala Asp Ser Val
    50                  55                  60

Lys Gly Arg Phe Thr Ile Ser Arg Asp Asn Ser Lys Asn Thr Val Tyr
65                  70                  75                  80

Leu Glu Met Ser Arg Leu Arg Ser Glu Asp Thr Ala Val Tyr Phe Cys
                85                  90                  95

Ala Lys Asp Arg Phe Thr Gly Asn His Tyr Tyr Gly Met Asp Val Trp
            100                 105                 110

Gly Gln Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacct tcagtatcta tggc                                          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Ile Tyr Gly
 1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
atttcagatg atggaagtga taag                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Asp Asp Gly Ser Asp Lys
 1               5

<210> SEQ ID NO 279
<211> LENGTH: 45
<212> TYPE: DNA
<213> ORGANISM: Artificial Sequence
<220> FEATURE:
<223> OTHER INFORMATION: Synthetic

<400> SEQUENCE: 279
gcgaaagacc ggtttactgg aaaccactat tacggtatgg acgtc                   45

<210> SEQ ID NO 280
<211> LENGTH: 15
<212> TYPE: PRT
<213> ORGANISM: Artificial Sequence
<220> FEATURE:
<223> OTHER INFORMATION: Synthetic

<400> SEQUENCE: 280

Ala Lys Asp Arg Phe Thr Gly Asn His Tyr Tyr Gly Met Asp Val
 1               5                  10                  15

<210> SEQ ID NO 281

<211> LENGTH: 321
<212> TYPE: DNA
<213> ORGANISM: Artificial Sequence
<220> FEATURE:
<223> OTHER INFORMATION: Synthetic

<400> SEQUENCE: 281

```
gacatccaga tgacccagtc tccatcctca ctgtctgcat ctgtaggaga cagagtcagt    60
atcacttgtc gggcgagtca ggacattagc gattatttag cctggtttca gcagaaacca   120
gggaaagccc ctaagtccct gatctatgct gcatccattt tgcaaaatgg ggtcccatca   180
aggttcagcg gcagtggatc tgggacagat ttcactctca ccatcagcag cctgcagcct   240
gaagattttg ctctttatta ctgtcatcag tataatcgtt tcccgtggac gttcggccaa   300
gggaccaagg tggaaatcaa a                                             321
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Ser Leu Ser Ala Ser Val Gly
 1               5                  10                  15

Asp Arg Val Ser Ile Thr Cys Arg Ala Ser Gln Asp Ile Ser Asp Tyr
             20                  25                  30

Leu Ala Trp Phe Gln Gln Lys Pro Gly Lys Ala Pro Lys Ser Leu Ile
         35                  40                  45

Tyr Ala Ala Ser Ile Leu Gln Asn Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Leu Tyr Tyr Cys His Gln Tyr Asn Arg Phe Pro Trp
                 85                  90                  95

Thr Phe Gly Gln Gly Thr Lys Val Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
caggacatta gcgattat                                                  18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Asp Ile Ser Asp Tyr
 1               5

<210> SEQ ID NO 285
<211> LENGTH: 9

<212> TYPE: DNA
<213> ORGANISM: Artificial Sequence
<220> FEATURE:
<223> OTHER INFORMATION: Synthetic

<400> SEQUENCE: 285 gctgcatcc                                                                9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
catcagtata atcgtttccc gtggacg                                           27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

His Gln Tyr Asn Arg Phe Pro Trp Thr
 1               5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
caggtgcagc tggtggagtc tgggggaggc gtggtccagc ctgggggtc cctgagactc        60 tcgtgtgcag cctctggatt cacgttcagt atctatggca tacactgggt ccgccaggct      120
ccaggcaagg gactggagtg gtggcagtc atatctgatg atggaagtaa taaaagtat       180 gcagactccg tgaagggccg attcaccatc tccagagaca attccaagaa cacgctgtat      240
ctgcaaatga acagcctgag agctgaggac acggctatat tttactgtgc gaaagatcgg      300
ataactggaa cccactacta cggaatggac gtctggggcc aagggaccac ggtcaccgtc      360
tcctca                                                                366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

| Gln | Val | Gln | Leu | Val | Glu | Ser | Gly | Gly | Val | Val | Gln | Pro | Gly | Gly |
|---|---|---|---|---|---|---|---|---|---|---|---|---|---|---|
| 1 | | | | 5 | | | | | 10 | | | | | 15 |

Ser Leu Arg Leu Ser Cys Ala Ala Ser Gly Phe Thr Phe Ser Ile Tyr
              20              25              30

Gly Ile His Trp Val Arg Gln Ala Pro Gly Lys Gly Leu Glu Trp Val
              35              40              45

Ala Val Ile Ser Asp Asp Gly Ser Asn Lys Lys Tyr Ala Asp Ser Val
 50                  55              60

Lys Gly Arg Phe Thr Ile Ser Arg Asp Asn Ser Lys Asn Thr Leu Tyr
 65                  70              75              80

Leu Gln Met Asn Ser Leu Arg Ala Glu Asp Thr Ala Ile Phe Tyr Cys
              85              90              95

Ala Lys Asp Arg Ile Thr Gly Thr His Tyr Tyr Gly Met Asp Val Trp
           100             105           110

Gly Gln Gly Thr Thr Val Thr Val Ser Ser
        115              120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacgt tcagtatcta tggc    24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ile Tyr Gly
1             5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atatctgatg atggaagtaa taaa    24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Asp Asp Gly Ser Asn Lys
1             5

<210> SEQ ID NO 295
<211> LENGTH: 45

<212> TYPE: DNA
<213> ORGANISM: Artificial Sequence
<220> FEATURE:
<223> OTHER INFORMATION: Synthetic

<400> SEQUENCE: 295
gcgaaagatc ggataactgg aacccactac tacggaatgg acgtc     45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Ala Lys Asp Arg Ile Thr Gly Thr His Tyr Tyr Gly Met Asp Val
 1               5                  10                  15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctca ctgtctgcat ctgtaggaga cagagtcagc     60
atcacttgtc gggcgagtca ggacattagc aattatttag cctggtttca gcagaaacca    120
gggaaagccc ctaagtccct gatctatgct gcttccagtt tgcaaagtgg ggtcccatca    180
aaattcagcg gcagtggatc tgggatagaa ttcactctca ccatcagcag cctgcagcct    240
gaagattttt caacttatta ctgccatcaa tataatcgtt tcccgtggac gttcggccaa    300
gggaccaagg tggaaatcaa a                                              321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
 1               5                  10                  15

Asp Arg Val Ser Ile Thr Cys Arg Ala Ser Gln Asp Ile Ser Asn Tyr
                20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
        50                  55                  60

Ser Gly Ser Gly Ile Glu Phe Thr Leu Thr Ile Ser Ser Leu Gln Pro
 65                 70                  75                  80

Glu Asp Phe Ser Thr Tyr Tyr Cys His Gln Tyr Asn Arg Phe Pro Trp
                85                  90                  95

Thr Phe Gly Gln Gly Thr Lys Val Glu Ile Lys
            100                 105

<210> SEQ ID NO 299
<211> LENGTH: 18
<212> TYPE: DNA

```
<213> ORGANISM: Artificial Sequence
<220> FEATURE:
<223> OTHER INFORMATION: Synthetic

<400> SEQUENCE: 299
caggacatta gcaattat                                                     18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Ser Asn Tyr
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcttcc                                                                9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
catcaatata atcgtttccc gtggacg                                           27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

His Gln Tyr Asn Arg Phe Pro Trp Thr
 1               5

<210> SEQ ID NO 305
<211> LENGTH: 366
<212> TYPE: DNA
<213> ORGANISM: Artificial Sequence
<220> FEATURE:
<223> OTHER INFORMATION: Synthetic
```

-continued

```
<400> SEQUENCE: 305
gaggtgcagc tggtggagtc tgggggaggc ttggtccagc ctgggggtc  cctgaggctc      60 tcatgtgcag cctctagatt caccttact  aactattgga tgagttgggt  ccgccaggct    120
ccagggaagg ggctggagtg ggtggccaaa ataaagcaag atggaagtga gaaatactat    180
ctggactctg tgaaggaccg attcaccatc tccagagaca acgccaagaa ctcactttat    240
ctgcaaatga acagcctgag agccgaggac acggctgtgt attactgtgc gagtagcagc    300
agctggtacg actactacta cggtatggac gtctggggcc acgggaccac ggtcaccgtc    360
tcctca                                                                366

<210> SEQ ID NO 306
<211> LENGTH: 122
<212> TYPE: PRT
<213> ORGANISM: Artificial Sequence
<220> FEATURE:
<223> OTHER INFORMATION: Synthetic

<400> SEQUENCE: 306

Glu Val Gln Leu Val Glu Ser Gly Gly Gly Leu Val Gln Pro Gly Gly
 1               5                  10                  15

Ser Leu Arg Leu Ser Cys Ala Ala Ser Arg Phe Thr Phe Thr Asn Tyr
            20                  25                  30

Trp Met Ser Trp Val Arg Gln Ala Pro Gly Lys Gly Leu Glu Trp Val
        35                  40                  45

Ala Lys Ile Lys Gln Asp Gly Ser Glu Lys Tyr Tyr Leu Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Ser Ser Ser Trp Tyr Asp Tyr Tyr Tyr Gly Met Asp Val Trp
            100                 105                 110

Gly His Gly Thr Thr Val Thr Val Ser Ser
        115                 120

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
agattcacct ttactaacta ttgg                                              24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Arg Phe Thr Phe Thr Asn Tyr Trp
 1               5

<210> SEQ ID NO 309
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 309
ataaagcaag atggaagtga gaaa                                             24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Lys Gln Asp Gly Ser Glu Lys
 1               5

<210> SEQ ID NO 311
<211> LENGTH: 45
<212> TYPE: DNA
<213> ORGANISM: Artificial Sequence
<220> FEATURE:
<223> OTHER INFORMATION: Synthetic

<400> SEQUENCE: 311
gcgagtagca gcagctggta cgactactac tacggtatgg acgtc                      45

<210> SEQ ID NO 312
<211> LENGTH: 15
<212> TYPE: PRT
<213> ORGANISM: Artificial Sequence
<220> FEATURE:
<223> OTHER INFORMATION: Synthetic

<400> SEQUENCE: 312

Ala Ser Ser Ser Ser Trp Tyr Asp Tyr Tyr Tyr Gly Met Asp Val
 1               5                  10                  15

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gaaattgtgt tgactcagtc tccagacttt cagtctgtga ctccaaaaga gaaagtcacc      60
atcacctgcc gggccagtca gagcattggt actaacttac actggtacca gcagagacca     120
gatcagtctc caaagctcct catcaagttt gcttcccagt ccttctcagg ggtcccctcg     180
aggttcagtg gcagtggatc tgggacagat ttcaccctca ccatcaatag cctggaagct     240
gaagatgctg caacgtatta ctgtcatcag actaactttt acctcacac tttcggcgga     300 gggaccaagg tggaaatcaa acga                                            324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Glu Ile Val Leu Thr Gln Ser Pro Asp Phe Gln Ser Val Thr Pro Lys
```

```
                1               5                   10                  15
            Glu Lys Val Thr Ile Thr Cys Arg Ala Ser Gln Ser Ile Gly Thr Asn
                            20                  25                  30

Leu His Trp Tyr Gln Gln Arg Pro Asp Gln Ser Pro Lys Leu Leu Ile
                        35                  40                  45

Lys Phe Ala Ser Gln Ser Phe Ser Gly Val Pro Ser Arg Phe Ser Gly
                    50                  55                  60

Ser Gly Ser Gly Thr Asp Phe Thr Leu Thr Ile Asn Ser Leu Glu Ala
             65                  70                  75                  80

Glu Asp Ala Ala Thr Tyr Tyr Cys His Gln Thr Asn Phe Leu Pro His
                            85                  90                  95

Thr Phe Gly Gly Gly Thr Lys Val Glu Ile Lys Arg
                        100                 105
```

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagagcattg gtactaac                                               18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Ser Ile Gly Thr Asn
 1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 tttgcttcc                                                          9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Phe Ala Ser
 1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
catcagacta acttttttacc tcacact 27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

His Gln Thr Asn Phe Leu Pro His Thr
1               5

<210> SEQ ID NO 321
<211> LENGTH: 366
<212> TYPE: DNA
<213> ORGANISM: Artificial Sequence
<220> FEATURE:
<223> OTHER INFORMATION: Synthetic

<400> SEQUENCE: 321
caggtgcagc tggtggagtc tgggggaggc gtggtccagc ctgggaggtc cctgagactc    60
tcctgtgcag cctctggatt caccttcagt aactatggca tgtactgggt ccgccaggct   120
ccaggcaagg ggctggagtg ggtgacattc atatcatatg atggaagtaa taaaaactat   180
gtagactcca tgaagggccg attcaccatc tccagagaca attccaagaa cacgctgtat   240
ctgcaaatga acagtctgag agttgaggac acggctgtat attactgtgc gaaagatcgt   300
ataagtggaa ctccatggta cggtatggac gtctggggcc aagggaccac ggtcaccgtc   360
tcctca                                                             366

<210> SEQ ID NO 322
<211> LENGTH: 122
<212> TYPE: PRT
<213> ORGANISM: Artificial Sequence
<220> FEATURE:
<223> OTHER INFORMATION: Synthetic

<400> SEQUENCE: 322

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Thr Phe Ile Ser Tyr Asp Gly Ser Asn Lys Asn Tyr Val Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Arg Ile Ser Gly Thr Pro Trp Tyr Gly Met Asp Val Trp
            100                 105                 110

Gly Gln Gly Thr Thr Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct tcagtaacta tggc        24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Ser Asn Tyr Gly
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
atatcatatg atggaagtaa taaa        24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Tyr Asp Gly Ser Asn Lys
1               5

<210> SEQ ID NO 327
<211> LENGTH: 45
<212> TYPE: DNA
<213> ORGANISM: Artificial Sequence
<220> FEATURE:
<223> OTHER INFORMATION: Synthetic

<400> SEQUENCE: 327
gcgaaagatc gtataagtgg aactccatgg tacggtatgg acgtc        45

<210> SEQ ID NO 328
<211> LENGTH: 15
<212> TYPE: PRT
<213> ORGANISM: Artificial Sequence
<220> FEATURE:
<223> OTHER INFORMATION: Synthetic

<400> SEQUENCE: 328

Ala Lys Asp Arg Ile Ser Gly Thr Pro Trp Tyr Gly Met Asp Val
1               5                   10                  15

<210> SEQ ID NO 329
<211> LENGTH: 321
<212> TYPE: DNA
<213> ORGANISM: Artificial Sequence
<220> FEATURE:
<223> OTHER INFORMATION: Synthetic

<400> SEQUENCE: 329

```
gacatccaga tgacccagtc tccatcctca ctgtctgcat ctgtaggaga cagagtcacc        60
atcacttgtc gggcgagtca ggacattgcc gattatttag cctggtttca acagaaacca       120
gggaaagccc ctaagtccct gatctttgct gcatccagtc tggaaagttg ggttcccta        180 aagttcagcg gcagtggatc tgggacagat ttcactctca ccatcagcag cctgcagcct       240
gaagattttg caacttatta ctgccaacag tatagtaggt tcccgatcac cttcggccaa       300
gggaccaagg tggaaatcaa a                                                 321
```

<210> SEQ ID NO 330
<211> LENGTH: 107
<212> TYPE: PRT
<213> ORGANISM: Artificial Sequence
<220> FEATURE:
<223> OTHER INFORMATION: Synthetic

<400> SEQUENCE: 330

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ala Asp Tyr
            20                  25                  30

Leu Ala Trp Phe Gln Gln Lys Pro Gly Lys Ala Pro Lys Ser Leu Ile
        35                  40                  45

Phe Ala Ala Ser Ser Leu Glu Ser Trp Val Pro Leu Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Arg Phe Pro Ile
                85                  90                  95

Thr Phe Gly Gln Gly Thr Lys Val Glu Ile Lys
            100                 105
```

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331
caggacattg ccgattat                                                      18

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

```
Gln Asp Ile Ala Asp Tyr
 1               5
```

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Ala Ala Ser
 1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
caacagtata gtaggttccc gatcacc                                         27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln Tyr Ser Arg Phe Pro Ile Thr
 1               5

<210> SEQ ID NO 337
<211> LENGTH: 366
<212> TYPE: DNA
<213> ORGANISM: Artificial Sequence
<220> FEATURE:
<223> OTHER INFORMATION: Synthetic

<400> SEQUENCE: 337
caggtgcagc tggtggagtc tgggggaggc gtggtccagc ctggggaggtc cctgagactc      60 tcctgtgcag cctctggatt caccttcagt aactatggca tgcactgggt ccgccaggct     120
ccaggcaagg ggctggagtg ggtgacactc atagaacatg atggaagtaa taaaaactat     180
gtagactccg tgaagggccg attcaccatc tccagagaca attccaagaa cacgctgtat     240
ctgcaaatga acagtctgag agttgaggac acggctgtat attactgtgc gaaagatcgt     300
ataactggaa ctccatggta cggtatggac gtctggggcc aagggaccac ggtcaccgtc     360
tcctca                                                                366

<210> SEQ ID NO 338
<211> LENGTH: 122
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

```
Gly Met His Trp Val Arg Gln Ala Pro Gly Lys Gly Leu Glu Trp Val
            35                  40                  45

Thr Leu Ile Glu His Asp Gly Ser Asn Lys Asn Tyr Val Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Lys Asp Arg Ile Thr Gly Thr Pro Trp Tyr Gly Met Asp Val Trp
                100                 105                 110

Gly Gln Gly Thr Thr Val Thr Val Ser Ser
            115                 120

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacct tcagtaacta tggc                                    24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Phe Ser Asn Tyr Gly
  1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atagaacatg atggaagtaa taaa                                    24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Glu His Asp Gly Ser Asn Lys
  1               5

<210> SEQ ID NO 343
<211> LENGTH: 45
<212> TYPE: DNA
<213> ORGANISM: Artificial Sequence
<220> FEATURE:
<223> OTHER INFORMATION: Synthetic

<400> SEQUENCE: 343
```

```
gcgaaagatc gtataactgg aactccatgg tacggtatgg acgtc                      45
```

<210> SEQ ID NO 344
<211> LENGTH: 15
<212> TYPE: PRT
<213> ORGANISM: Artificial Sequence
<220> FEATURE:
<223> OTHER INFORMATION: Synthetic

<400> SEQUENCE: 344

```
Ala Lys Asp Arg Ile Thr Gly Thr Pro Trp Tyr Gly Met Asp Val
 1               5                  10                  15
```

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345

```
gacatccaga tgacccagtc tccatcctca ctgtctgcat ctgtaggaga cagagtcacc      60
atcacttgtc gggcgagtca ggacattgcc gattatttag cctggtttca acagaaacca    120
gggaaagccc ctaaatccct gatctttgcg gcatccagtc tggaaagttg ggttccctta    180
aagttcagcg gcagtggatc tgggacagat ttcactctca ccatcagcag cctgcagcct    240
gaagattttg caacttatta ctgccaacag tataataggt tcccgatcac cttcggccaa    300
gggacacgac tggagattaa a                                              321
```

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ala Asp Tyr
                20                  25                  30

Leu Ala Trp Phe Gln Gln Lys Pro Gly Lys Ala Pro Lys Ser Leu Ile
            35                  40                  45

Phe Ala Ala Ser Ser Leu Glu Ser Trp Val Pro Leu Lys Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Arg Phe Pro Ile
                85                  90                  95

Thr Phe Gly Gln Gly Thr Arg Leu Glu Ile Lys
            100                 105
```

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347

```
caggacattg ccgattat                                                   18
```

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Asp Ile Ala Asp Tyr
 1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 gcggcatcc                                                                  9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Ala Ala Ser
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagtata ataggttccc gatcacc                                             27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Asn Arg Phe Pro Ile Thr
 1               5

<210> SEQ ID NO 353
<211> LENGTH: 366
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtccagc ctggggggtc cctgaggctc         60
tcatgtgcag cctctagatt cacctttagt acctattgga tgagctgggt ccgccaggct        120
ccagggaagg ggctggagtg ggtggccaaa ataaagcaag atggaagtga gaaatactat        180

```
ctggactctg tgaaggaccg attcaccatc tccagagaca acgccaagaa ctcactgtat    240
ctgcaaatga acagcctgag agccgaagac acggctgtgt attactgtgc gagtagcatt    300
acctggtacg actactacta cggtatggac gtctggggcc acgggaccac ggtcaccgtc    360
tcctca                                                               366
```

```
<210> SEQ ID NO 354
<211> LENGTH: 122
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
  1               5                  10                  15

Ser Leu Arg Leu Ser Cys Ala Ala Ser Arg Phe Thr Phe Ser Thr Tyr
             20                  25                  30

Trp Met Ser Trp Val Arg Gln Ala Pro Gly Lys Gly Leu Glu Trp Val
         35                  40                  45

Ala Lys Ile Lys Gln Asp Gly Ser Glu Lys Tyr Tyr Leu Asp Ser Val
     50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ser Ser Ile Thr Trp Tyr Asp Tyr Tyr Tyr Gly Met Asp Val Trp
            100                 105                 110

Gly His Gly Thr Thr Val Thr Val Ser Ser
        115                 120
```

```
<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
agattcacct ttagtaccta ttgg                                            24
```

```
<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Arg Phe Thr Phe Ser Thr Tyr Trp
  1               5
```

```
<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
ataaagcaag atggaagtga gaaa                                            24
```

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Ile Lys Gln Asp Gly Ser Glu Lys
 1               5

<210> SEQ ID NO 359
<211> LENGTH: 45
<212> TYPE: DNA
<213> ORGANISM: Artificial Sequence
<220> FEATURE:
<223> OTHER INFORMATION: Synthetic

<400> SEQUENCE: 359
gcgagtagca ttacctggta cgactactac tacggtatgg acgtc                    45

<210> SEQ ID NO 360
<211> LENGTH: 15
<212> TYPE: PRT
<213> ORGANISM: Artificial Sequence
<220> FEATURE:
<223> OTHER INFORMATION: Synthetic

<400> SEQUENCE: 360

Ala Ser Ser Ile Thr Trp Tyr Asp Tyr Tyr Tyr Gly Met Asp Val
 1               5                  10                  15

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361
gaaattgtgt tgacgcagtc tccagacttt cagtctgtga ctccaaaaga gaaagtcacc     60
atcacctgcc gggccagtca gagcattggt agtaacttac actggtacca gcagaaacca    120
gatcagtctc caaacctcct catcaagttt gcttcccagt ccttctcagg ggtcccctcg    180
aggttcagtg gcagtggatc tgggacagat ttcaccctca ccatcaatag cctggaagct    240
gaagatgctg caacgtatta ctgtcatcag actaattttt acctcacac tttcggcgga    300 gggaccaagg tggaaatcaa a                                              321

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Asn
            20                  25                  30

Leu His Trp Tyr Gln Gln Lys Pro Asp Gln Ser Pro Asn Leu Leu Ile
        35                  40                  45

Lys Phe Ala Ser Gln Ser Phe Ser Gly Val Pro Ser Arg Phe Ser Gly
         50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Thr Asn Phe Leu Pro His
                 85                  90                  95

Thr Phe Gly Gly Gly Thr Lys Val Glu Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagcattg gtagtaac                                                 18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

Gln Ser Ile Gly Ser Asn
 1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 tttgcttcc                                                            9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Phe Ala Ser
 1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
catcagacta attttttacc tcacact                                       27

<210> SEQ ID NO 368
<211> LENGTH: 9
<212> TYPE: PRT

<213> ORGANISM: Artificial Sequence
<220> FEATURE:
<223> OTHER INFORMATION: Synthetic

<400> SEQUENCE: 368

His Gln Thr Asn Phe Leu Pro His Thr
1               5

<210> SEQ ID NO 369
<211> LENGTH: 366
<212> TYPE: DNA
<213> ORGANISM: Artificial Sequence
<220> FEATURE:
<223> OTHER INFORMATION: Synthetic

<400> SEQUENCE: 369
caggtgcagc tggtggagtc tgggggaggc gtggtccagc ctgggaggtc cctgagactc      60
tcctgtgcag cctctggatt caccttcagt atctatggca tgaactgggt ccgccagggt     120
ccaggcaagg ggctggactg ggtggcagtt atttcagatg atggaagtaa taaagactat     180
gtagactccg tgaggggtcg attcaccatc tccagagaca attccaagaa cacgctgtat     240
ctgcaaatga acagcctgag cgctgaagac acggctgtct attactgtgc gaaagatcgt     300
atcactggca ctcattacta cggtatggac gtctggggcc aagggaccac ggtcaccgtc     360
tcctca                                                               366

<210> SEQ ID NO 370
<211> LENGTH: 122
<212> TYPE: PRT
<213> ORGANISM: Artificial Sequence
<220> FEATURE:
<223> OTHER INFORMATION: Synthetic

<400> SEQUENCE: 370

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met Asn Trp Val Arg Gln Gly Pro Gly Lys Gly Leu Asp Trp Val
        35                  40                  45

Ala Val Ile Ser Asp Asp Gly Ser Asn Lys Asp Tyr Val Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95

Ala Lys Asp Arg Ile Thr Gly Thr His Tyr Tyr Gly Met Asp Val Trp
            100                 105                 110

Gly Gln Gly Thr Thr Val Thr Val Ser Ser
        115                 120

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcacct tcagtatcta tggc                                            24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Phe Thr Phe Ser Ile Tyr Gly
1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
atttcagatg atggaagtaa taaa                                              24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Asp Asp Gly Ser Asn Lys
1               5

<210> SEQ ID NO 375
<211> LENGTH: 45
<212> TYPE: DNA
<213> ORGANISM: Artificial Sequence
<220> FEATURE:
<223> OTHER INFORMATION: Synthetic

<400> SEQUENCE: 375
gcgaaagatc gtatcactgg cactcattac tacggtatgg acgtc                       45

<210> SEQ ID NO 376
<211> LENGTH: 15
<212> TYPE: PRT
<213> ORGANISM: Artificial Sequence
<220> FEATURE:
<223> OTHER INFORMATION: Synthetic

<400> SEQUENCE: 376

Ala Lys Asp Arg Ile Thr Gly Thr His Tyr Tyr Gly Met Asp Val
1               5                   10                  15

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccgtcctca ctgtctgcat ctgtcggaga cagaatcacc       60
atcacttgtc gggcgagtca ggacattgcc aattatttag cctggtttca gcagaaacca     120
ggtaatgccc ctacgtccct gatctatgct gcatccattt tgcaaagtgg ggtcccatca     180

```
aagttcagcg gcagtggatc tgggacagat tcactctca ccatcaccag cctgcagcca    240
gaagattttg caagttatta ctgccaacaa tataatagaa agccgtggac gttcggccga    300
gggaccaagg tggaaatcaa a                                              321
```

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

```
Asp Ile Gln Met Thr Gln Ser Pro Ser Ser Leu Ser Ala Ser Val Gly
  1               5                  10                  15

Asp Arg Ile Thr Ile Thr Cys Arg Ala Ser Gln Asp Ile Ala Asn Tyr
             20                  25                  30

Leu Ala Trp Phe Gln Gln Lys Pro Gly Asn Ala Pro Thr Ser Leu Ile
         35                  40                  45

Tyr Ala Ala Ser Ile Leu Gln Ser Gly Val Pro Ser Lys Phe Ser Gly
     50                  55                  60

Ser Gly Ser Gly Thr Asp Phe Thr Leu Thr Ile Thr Ser Leu Gln Pro
 65                  70                  75                  80

Glu Asp Phe Ala Ser Tyr Tyr Cys Gln Gln Tyr Asn Arg Lys Pro Trp
                 85                  90                  95

Thr Phe Gly Arg Gly Thr Lys Val Glu Ile Lys
            100                 105
```

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379

```
caggacattg ccaattat                                                  18
```

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

```
Gln Asp Ile Ala Asn Tyr
  1               5
```

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381

```
gctgcatcc                                                             9
```

<210> SEQ ID NO 382
<211> LENGTH: 3
<212> TYPE: PRT
<213> ORGANISM: Artificial Sequence

```
<220> FEATURE:
<223> OTHER INFORMATION: Synthetic

<400> SEQUENCE: 382

Ala Ala Ser
 1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacaatata atagaaagcc gtggacg                                              27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Tyr Asn Arg Lys Pro Trp Thr
 1               5

<210> SEQ ID NO 385
<211> LENGTH: 1210
<212> TYPE: PRT
<213> ORGANISM: Homo sapiens

<400> SEQUENCE: 385

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205
```

```
Lys Leu Thr Lys Ile Ile Cys Ala Gln Gln Cys Ser Gly Arg Cys Arg
            210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
            245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
            290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
            325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
            370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
```

-continued

```
Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
        1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
```

```
                    1045                1050                1055
Ser Cys Pro Ile Lys Glu Asp Ser Phe Leu Gln Arg Tyr Ser Ser Asp
                1060                1065                1070

Pro Thr Gly Ala Leu Thr Glu Asp Ser Ile Asp Asp Thr Phe Leu Pro
            1075                1080                1085

Val Pro Glu Tyr Ile Asn Gln Ser Val Pro Lys Arg Pro Ala Gly Ser
        1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165

Asn Pro Asp Tyr Gln Gln Asp Phe Phe Pro Lys Glu Ala Lys Pro Asn
        1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 386
<211> LENGTH: 660
<212> TYPE: PRT
<213> ORGANISM: Artificial Sequence
<220> FEATURE:
<223> OTHER INFORMATION: Synthetic

<400> SEQUENCE: 386

Leu Glu Glu Lys Lys Val Cys Gln Gly Thr Ser Asn Lys Leu Thr Gln
 1                5                  10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
```

```
            195                 200                 205
His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
            290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
                500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
                580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Cys
610                 615                 620
```

```
Pro Gly Gly Glu Gln Lys Leu Ile Ser Glu Asp Leu Gly Gly Glu
625                 630                 635                 640

Gln Lys Leu Ile Ser Glu Glu Asp Leu Ser Gly His His His His
                645                 650                 655

His Ser Ser Gly
            660

<210> SEQ ID NO 387
<211> LENGTH: 856
<212> TYPE: PRT
<213> ORGANISM: Homo sapiens

<400> SEQUENCE: 387

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
```

```
                    325                 330                 335
Asn Cys Thr Ser Ile Ser Gly Asp Leu His Ile Leu Pro Val Ala Phe
                340                 345                 350
Arg Gly Asp Ser Phe Thr His Thr Pro Pro Leu Asp Pro Gln Glu Leu
                355                 360                 365
Asp Ile Leu Lys Thr Val Lys Glu Ile Thr Gly Phe Leu Leu Ile Gln
                370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
                420                 425                 430
Ser Asp Gly Asp Val Ile Ile Ser Gly Asn Lys Asn Leu Cys Tyr Ala
                435                 440                 445
Asn Thr Ile Asn Trp Lys Lys Leu Phe Gly Thr Ser Gly Gln Lys Thr
                450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
                515                 520                 525
Ser Glu Cys Ile Gln Cys His Pro Glu Cys Leu Pro Gln Ala Met Asn
                530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Cys Thr Gly Pro Gly
                595                 600                 605
Leu Glu Gly Cys Pro Thr Asn Gly Pro Lys Ile Pro Ser Ile Ala Glu
                610                 615                 620
Pro Arg Gly Pro Thr Ile Lys Pro Cys Pro Pro Cys Lys Cys Pro Ala
625                 630                 635                 640
Pro Asn Leu Leu Gly Gly Pro Ser Val Phe Ile Phe Pro Pro Lys Ile
                645                 650                 655
Lys Asp Val Leu Met Ile Ser Leu Ser Pro Ile Val Thr Cys Val Val
                660                 665                 670
Val Asp Val Ser Glu Asp Asp Pro Asp Val Gln Ile Ser Trp Phe Val
                675                 680                 685
Asn Asn Val Glu Val His Thr Ala Gln Thr Gln Thr His Arg Glu Asp
                690                 695                 700
Tyr Asn Ser Thr Leu Arg Val Val Ser Ala Leu Pro Ile Gln His Gln
705                 710                 715                 720
Asp Trp Met Ser Gly Lys Glu Phe Lys Cys Lys Val Asn Asn Lys Asp
                725                 730                 735
Leu Pro Ala Pro Ile Glu Arg Thr Ile Ser Lys Pro Lys Gly Ser Val
                740                 745                 750
```

-continued

```
Arg Ala Pro Gln Val Tyr Val Leu Pro Pro Glu Glu Glu Met Thr
        755                 760                 765
Lys Lys Gln Val Thr Leu Thr Cys Met Val Thr Asp Phe Met Pro Glu
    770                 775                 780
Asp Ile Tyr Val Glu Trp Thr Asn Asn Gly Lys Thr Glu Leu Asn Tyr
785                 790                 795                 800
Lys Asn Thr Glu Pro Val Leu Asp Ser Asp Gly Ser Tyr Phe Met Tyr
                805                 810                 815
Ser Lys Leu Arg Val Glu Lys Lys Asn Trp Val Glu Arg Asn Ser Tyr
            820                 825                 830
Ser Cys Ser Val Val His Glu Gly Leu His Asn His His Thr Thr Lys
        835                 840                 845
Ser Phe Ser Arg Thr Pro Gly Lys
    850                 855

<210> SEQ ID NO 388
<211> LENGTH: 227
<212> TYPE: PRT
<213> ORGANISM: Homo sapiens

<400> SEQUENCE: 388

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
            85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225
```